United States Patent
Reed et al.

(10) Patent No.: US 7,521,548 B2
(45) Date of Patent: Apr. 21, 2009

(54) APOPTOSIS MODULATOR BCL-B AND METHODS FOR MAKING AND USING SAME

(75) Inventors: John C. Reed, Rancho Santa Fe, CA (US); Ning Ke, San Diego, CA (US); Adam Godzik, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 350 days.

(21) Appl. No.: 10/071,174

(22) Filed: Feb. 7, 2002

(65) Prior Publication Data

US 2003/0176671 A1 Sep. 18, 2003

Related U.S. Application Data

(60) Provisional application No. 60/267,166, filed on Feb. 7, 2001.

(51) Int. Cl.
  *C07H 21/04* (2006.01)
(52) U.S. Cl. ..................... 536/23.5; 435/69.1
(58) Field of Classification Search ............... 536/23.1, 536/24.33, 24.31, 24.3, 235; 435/320.1, 435/252.3, 325, 69.1
See application file for complete search history.

(56) References Cited

U.S. PATENT DOCUMENTS 6,582,908 B2 * 6/2003 Fodor et al. ................ 506/9

FOREIGN PATENT DOCUMENTS

WO    WO 00/00506    *    1/2000

OTHER PUBLICATIONS

Anderson (Nature 1998; 392(suppl):25-30).*
Dang et al. (Clinical Cancer Research 1999; 5:471-474).*
Levine et al. (Molecular Medicine Today 1999; 5:165-171).*
Ke et al.; Bcl-B, a Novel Bcl-2 Family Member That Differentially Binds and Regulates Bax and Bak; The Journal of Biological Chemistry, vol. 276, No. 16; Apr. 2001; p. 12481-12484.
Aouacheria et al.; Nrh, a human homologue of Nr-13 associates with Bcl-Xs and is an inhibitor of apoptosis; Oncogene, vol. 20; 2001; p. 5846-5855.
Zhang et al.; Bcl2-L-10, a novel anti-apoptotic member of the Bcl-2 family, blocks apoptosis in the mitochondria death pathway but not in the death receptor pathway; Human Molecular Genetics, vol. 10, No. 21; 2001; p. 2329-2339.
Bouillet et al., BH3-only proteins—evolutionarily conserved pro-apoptotic Bcl-2 family members essential for initiating programmed cell death; Journal of Cell Science, vol. 115; 2002; p. 1567-1574.

* cited by examiner

*Primary Examiner*—J. E Angell
(74) *Attorney, Agent, or Firm*—Catalyst Law Group, APC; David M. Kohn

(57) ABSTRACT

A novel human member of the Bcl-2 family Bcl-B has been identified, which is closest in amino-acid sequence homology to the Boo (Diva) protein. The Bcl-B protein is widely expressed in adult human tissues. The Bcl-B protein modulates apoptosis. Bcl-B also binds Bcl-2, BCl-XL, and Bax but not Bak. Bcl-B displays a unique pattern of selectivity for binding and regulating the function of other members of the Bcl-2 family.

15 Claims, 5 Drawing Sheets

SEQUENCE LISTING

<160> NUMBER OF SEQ ID NOS: 36

<210> SEQ ID NO 1
<211> LENGTH: 887
<212> TYPE: DNA
<213> ORGANISM: Homo sapiens

<400> SEQUENCE: 1

```
cgggccaaga aaaccagcga aggcccggcc ccccagcaga ggccggacca tggttgacca      60
gttgcgggag cgcaccacca tggccgaccc gctgcgggag cgcaccgagc tgttgctggc     120
cgactacctg gggtactgcg cccgggaacc cggcacccc gagccggcgc catccacgcc      180
cgaggccgcc gtgctgcgct ccgcggccgc caggttacgg cagattcacc ggtccttttt     240
ctccgcctac ctcggctacc ccgggaaccg cttcgagctg gtggcgctga tggcggattc     300
cgtgctctcc gacagccccg gccccacctg gggcagagtg gtgacgctcg tgaccttcgc     360
agggacgctg ctggagagag ggccgctggt gaccgcccgg tggaagaagt ggggcttcca     420
gccgcggcta aaggagcagg agggcgacgt cgcccgggac tgccagcgcc tggtggcctt     480
gctgagctcg cggctcatgg ggcagcaccg cgcctggctg caggctcagg gcggctggga     540
tggcttttgt cacttcttca ggaccccctt tccactggct ttttggagaa aacagctggt     600
ccaggctttt ctgtcatgct tgttaacaac agccttcatt tatctctgga cacgattatt     660
atgagtttta aaacttttaa cccgcttcta cctgcccaac tgtgaccaac taaatgacag     720
atgtgtgaga acaagaactg agggaaagca ccttccccca ccccagacgt ttttatctga     780
atgcatacaa ggagtcctga ggtggtgatt tggccagtgt tttaacttgt gacaagtact     840
caggtgtgag gacaagaatg caaatggctc ttccttgagt gaaagaa                   887
```

<210> SEQ ID NO 2
<211> LENGTH: 204
<212> TYPE: PRT
<213> ORGANISM: Homo sapiens

<400> SEQUENCE: 2

```
Met Val Asp Gln Leu Arg Glu Arg Thr Thr Met Ala Asp Pro Leu Arg
  1               5                  10                  15

Glu Arg Thr Glu Leu Leu Leu Ala Asp Tyr Leu Gly Tyr Cys Ala Arg
             20                  25                  30

Glu Pro Gly Thr Pro Glu Pro Ala Pro Ser Thr Pro Glu Ala Ala Val
         35                  40                  45
```

```
Leu Arg Ser Ala Ala Ala Arg Leu Arg Gln Ile His Arg Ser Phe Phe
        50                  55                  60

Ser Ala Tyr Leu Gly Tyr Pro Gly Asn Arg Phe Glu Leu Val Ala Leu
 65                  70                  75                  80

Met Ala Asp Ser Val Leu Ser Asp Ser Pro Gly Pro Thr Trp Gly Arg
                 85                  90                  95

Val Val Thr Leu Val Thr Phe Ala Gly Thr Leu Leu Glu Arg Gly Pro
                100                 105                 110

Leu Val Thr Ala Arg Trp Lys Lys Trp Gly Phe Gln Pro Arg Leu Lys
                115                 120                 125

Glu Gln Glu Gly Asp Val Ala Arg Asp Cys Gln Arg Leu Val Ala Leu
            130                 135                 140

Leu Ser Ser Arg Leu Met Gly Gln His Arg Ala Trp Leu Gln Ala Gln
145                 150                 155                 160

Gly Gly Trp Asp Gly Phe Cys His Phe Phe Arg Thr Pro Phe Pro Leu
                165                 170                 175

Ala Phe Trp Arg Lys Gln Leu Val Gln Ala Phe Leu Ser Cys Leu Leu
                180                 185                 190

Thr Thr Ala Phe Ile Tyr Leu Trp Thr Arg Leu Leu
                195                 200

<210> SEQ ID NO 3
<211> LENGTH: 21
<212> TYPE: PRT
<213> ORGANISM: Homo sapiens

<400> SEQUENCE: 3

Val Leu Ser Asp Ser Pro Gly Pro Thr Trp Gly Arg Val Val Thr Leu
 1               5                  10                  15

Val Thr Phe Ala Gly
                20

<210> SEQ ID NO 4
<211> LENGTH: 15
<212> TYPE: PRT
<213> ORGANISM: Homo sapiens

<400> SEQUENCE: 4

Ala Trp Leu Gln Ala Gln Gly Gly Trp Asp Gly Phe Cys His Phe
 1               5                  10                  15

<210> SEQ ID NO 5
<211> LENGTH: 15
<212> TYPE: PRT
<213> ORGANISM: Homo sapiens

<400> SEQUENCE: 5

Glu Ala Ala Val Leu Arg Ser Ala Ala Ala Arg Leu Arg Gln Ile
 1               5                  10                  15

<210> SEQ ID NO 6
<211> LENGTH: 21
<212> TYPE: PRT
<213> ORGANISM: Homo sapiens

<400> SEQUENCE: 6

Glu Arg Thr Glu Leu Leu Leu Ala Asp Tyr Leu Gly Tyr Cys Ala Arg
 1               5                  10                  15

Glu Pro Gly Thr Pro
                20
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
cgggccaaga aaaccagcga agg                                           23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
cactcaagga agagccattt gcat                                          24

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 9
ggaattcatg gttgaccagt tgcgggag                                      28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
ccgctcgagt cataataatc gtgtccagag                                    30

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 11
ccgctcgagt catgttttct ccaaaaagcc agtg                               34

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
gtggtgacgc tcgtgacctt cg                                            22

<210> SEQ ID NO 13
<211> LENGTH: 24
<212> TYPE: PRT
<213> ORGANISM: Homo sapiens

```
<400> SEQUENCE: 13

Leu Arg Glu Arg Thr Glu Leu Leu Ala Asp Tyr Leu Gly Tyr Cys
 1               5                  10                  15

Ala Arg Glu Pro Gly Thr Pro Glu
            20

<210> SEQ ID NO 14
<211> LENGTH: 24
<212> TYPE: PRT
<213> ORGANISM: Murine sp.

<400> SEQUENCE: 14

Leu His Glu Arg Thr Arg Arg Leu Leu Ser Asp Tyr Ile Phe Phe Cys
 1               5                  10                  15

Ala Arg Glu Pro Asp Thr Pro Glu
            20

<210> SEQ ID NO 15
<211> LENGTH: 22
<212> TYPE: PRT
<213> ORGANISM: Gallus sp.

<400> SEQUENCE: 15

Leu Lys Glu Glu Thr Ala Leu Leu Glu Asp Tyr Phe Gln His Arg
 1               5                  10                  15

Ala Gly Gly Ala Ala Leu
            20

<210> SEQ ID NO 16
<211> LENGTH: 24
<212> TYPE: PRT
<213> ORGANISM: Homo sapiens

<400> SEQUENCE: 16

Thr Gly Tyr Asp Asn Arg Glu Ile Val Met Lys Tyr Ile His Tyr Lys
 1               5                  10                  15

Leu Ser Gln Arg Gly Tyr Glu Trp
            20

<210> SEQ ID NO 17
<211> LENGTH: 24
<212> TYPE: PRT
<213> ORGANISM: Homo sapiens

<400> SEQUENCE: 17

Met Ser Gln Ser Asn Arg Glu Leu Val Val Asp Phe Leu Ser Tyr Lys
 1               5                  10                  15

Leu Ser Gln Lys Gly Tyr Ser Trp
            20

<210> SEQ ID NO 18
<211> LENGTH: 24
<212> TYPE: PRT
<213> ORGANISM: Caenorhabditis elegans

<400> SEQUENCE: 18

Pro Arg Leu Asp Ile Glu Gly Phe Val Val Asp Tyr Phe Thr His Arg
 1               5                  10                  15

Ile Arg Gln Asn Gly Met Glu Trp
            20
```

```
<210> SEQ ID NO 19
<211> LENGTH: 30
<212> TYPE: PRT
<213> ORGANISM: Homo sapiens

<400> SEQUENCE: 19

Met Ala Asp Ser Val Leu Ser Asp Ser Pro Gly Pro Thr Trp Gly Arg
1               5                   10                  15

Val Val Thr Leu Val Thr Phe Ala Gly Thr Leu Leu Glu Arg
            20                  25                  30

<210> SEQ ID NO 20
<211> LENGTH: 30
<212> TYPE: PRT
<213> ORGANISM: Murine sp.

<400> SEQUENCE: 20

Met Ala Asp Lys Leu Leu Ser Lys Asp Gln Asp Phe Ser Trp Ser Gln
1               5                   10                  15

Leu Val Met Leu Leu Ala Phe Ala Gly Thr Leu Met Asn Gln
            20                  25                  30

<210> SEQ ID NO 21
<211> LENGTH: 30
<212> TYPE: PRT
<213> ORGANISM: Gallus sp.

<400> SEQUENCE: 21

Lys Val Ala Ala Gln Leu Glu Thr Asp Gly Gly Leu Asn Trp Gly Arg
1               5                   10                  15

Leu Leu Ala Leu Val Val Phe Ala Gly Thr Leu Ala Ala Ala
            20                  25                  30

<210> SEQ ID NO 22
<211> LENGTH: 29
<212> TYPE: PRT
<213> ORGANISM: Homo sapiens

<400> SEQUENCE: 22

Thr Val Val Glu Glu Leu Phe Arg Asp Gly Val Asn Trp Gly Arg Ile
1               5                   10                  15

Val Ala Phe Phe Glu Phe Gly Gly Val Met Cys Val Glu
            20                  25

<210> SEQ ID NO 23
<211> LENGTH: 29
<212> TYPE: PRT
<213> ORGANISM: Homo sapiens

<400> SEQUENCE: 23

Gln Val Val Asn Glu Leu Phe Arg Asp Gly Val Asn Trp Gly Arg Ile
1               5                   10                  15

Val Ala Phe Phe Ser Phe Gly Gly Ala Leu Cys Val Glu
            20                  25

<210> SEQ ID NO 24
<211> LENGTH: 30
<212> TYPE: PRT
<213> ORGANISM: Caenorhabditis elegans

<400> SEQUENCE: 24

Thr Val Gly Asn Ala Gln Thr Asp Gln Cys Pro Met Ser Tyr Gly Arg
1               5                   10                  15
```

```
Leu Ile Gly Leu Ile Ser Phe Gly Gly Phe Val Ala Ala Lys
            20                  25                  30

<210> SEQ ID NO 25
<211> LENGTH: 22
<212> TYPE: PRT
<213> ORGANISM: Homo sapiens

<400> SEQUENCE: 25

Glu Ala Ala Val Leu Arg Ser Ala Ala Ala Arg Leu Arg Gln Ile His
1               5                   10                  15

Arg Ser Phe Phe Ser Ala
            20

<210> SEQ ID NO 26
<211> LENGTH: 25
<212> TYPE: PRT
<213> ORGANISM: Murine sp.

<400> SEQUENCE: 26

Thr Ser Val Glu Ala Ala Leu Leu Arg Ser Val Thr Arg Gln Ile Gln
1               5                   10                  15

Gln Glu His Gln Glu Phe Phe Ser Ser
            20                  25

<210> SEQ ID NO 27
<211> LENGTH: 25
<212> TYPE: PRT
<213> ORGANISM: Gallus sp.

<400> SEQUENCE: 27

Pro Ser Ala Thr Ala Ala Glu Leu Arg Arg Ala Ala Ala Glu Leu Glu
1               5                   10                  15

Arg Arg Glu Arg Pro Phe Phe Arg Ser
            20                  25

<210> SEQ ID NO 28
<211> LENGTH: 25
<212> TYPE: PRT
<213> ORGANISM: Homo sapiens

<400> SEQUENCE: 28

Pro Pro Val Val His Leu Thr Leu Arg Gln Ala Gly Asp Asp Phe Ser
1               5                   10                  15

Arg Arg Tyr Arg Arg Asp Phe Ala Glu
            20                  25

<210> SEQ ID NO 29
<211> LENGTH: 25
<212> TYPE: PRT
<213> ORGANISM: Homo sapiens

<400> SEQUENCE: 29

Met Ala Ala Val Lys Gln Ala Leu Arg Glu Ala Gly Asp Glu Phe Glu
1               5                   10                  15

Leu Arg Tyr Arg Arg Ala Phe Ser Asp
            20                  25

<210> SEQ ID NO 30
<211> LENGTH: 25
<212> TYPE: PRT
<213> ORGANISM: Caenorhabditis elegans
```

```
<400> SEQUENCE: 30

Val Gln Pro Glu His Glu Met Met Arg Val Met Gly Thr Ile Phe Glu
 1               5                  10                  15

Lys Lys His Ala Glu Asn Phe Glu Thr
            20                  25

<210> SEQ ID NO 31
<211> LENGTH: 18
<212> TYPE: PRT
<213> ORGANISM: Homo sapiens

<400> SEQUENCE: 31

Arg Ala Trp Leu Gln Ala Gln Gly Gly Trp Asp Gly Phe Cys His Phe
 1               5                  10                  15

Phe Arg

<210> SEQ ID NO 32
<211> LENGTH: 18
<212> TYPE: PRT
<213> ORGANISM: Murine sp.

<400> SEQUENCE: 32

Arg Ala Arg Leu Glu Ala Leu Gly Gly Trp Asp Gly Phe Cys Arg Phe
 1               5                  10                  15

Phe Lys

<210> SEQ ID NO 33
<211> LENGTH: 18
<212> TYPE: PRT
<213> ORGANISM: Gallus sp.

<400> SEQUENCE: 33

Gly Glu Trp Met Glu Glu His Gly Gly Trp Asp Gly Phe Cys Arg Phe
 1               5                  10                  15

Phe Gly

<210> SEQ ID NO 34
<211> LENGTH: 18
<212> TYPE: PRT
<213> ORGANISM: Homo sapiens

<400> SEQUENCE: 34

His Thr Trp Ile Gln Asp Asn Gly Gly Trp Asp Ala Phe Val Glu Leu
 1               5                  10                  15

Tyr Gly

<210> SEQ ID NO 35
<211> LENGTH: 18
<212> TYPE: PRT
<213> ORGANISM: Homo sapiens

<400> SEQUENCE: 35

Glu Pro Trp Ile Gln Glu Asn Gly Gly Trp Asp Thr Phe Val Glu Leu
 1               5                  10                  15

Tyr Gly

<210> SEQ ID NO 36
<211> LENGTH: 18
<212> TYPE: PRT
<213> ORGANISM: Caenorhabditis elegans
```

```
<400> SEQUENCE: 36

Asn Asn Trp Lys Glu His Asn Arg Ser Trp Asp Asp Phe Met Thr Leu
1               5                   10                  15

Gly Lys
```

APOPTOSIS MODULATOR BCL-B AND METHODS FOR MAKING AND USING SAME

This application claims priority to U.S. application serial No. 60/267,166, filed Feb. 7, 2001.

PRIORITY INFORMATION

This application was supported by NIH Grant GM60554 and by U.S. Army Medical Research and Material Command Grant DAMD17-99-1-9511.

TECHNICAL FIELD

This invention generally relates to cell and molecular biology and the regulation of cell proliferation, apoptosis and survival. In particular, the invention provides polypeptides comprising apoptosis modulator Bcl-B, a Bcl-2 family member, nucleic acids encoding the polypeptides, and methods for making and using these compositions, including, for example, modulating cell apoptosis, survival, proliferation.

BACKGROUND

Programmed cell death or apoptosis is a cellular suicide process in which damaged or harmful cells are eliminated from multicellular organisms. Cells undergoing apoptosis have distinct morphological changes including cell shrinkage, membrane blebbing, chromatin condensation, apoptotic body formation and protein and nucleic acid fragmentation. This cellular suicide program is evolutionarily conserved across animal and plant species.

Apoptosis plays an important role in the development and homeostasis of metazoans and is also important for insect embryonic development and metamorphosis. Furthermore, apoptosis can act as a host defense mechanism. For example, apoptosis eliminates virally infected cells thereby limiting propagation of viruses. Apoptosis is also involved in plant reactions to biotic and abiotic insults. Moreover, dysregulation of apoptosis has been associated with a variety of human diseases including cell proliferative disorders (e.g., cancer), cell degenerative disorders (e.g., neurodegeneration, muscular degeneration, ischemia, stroke, etc.) and autoimmune diseases. Accordingly, identification of the components that modulate apoptosis provides a means to study and manipulate the process in a wide variety of organisms.

Programmed cell death is regulated by the interplay of proteins that inhibit and proteins that stimulate cell death or cell survival. Among the proteins that modulate apoptosis are the Bcl-2 family members. Bcl-2 protein family members include proteins that promote and inhibit programmed cell death. Bcl-2 family proteins play a role in apoptosis regulation in metazoan species. In humans, over 20 Bcl-2 proteins have been identified to date, including proteins which suppress (Bcl-2, Bcl-XL, Mcl-1, Bfl-1/A1, Bcl-W) and proteins which promote (Bax, Bak, Bok, Bad, Bid, Bik, Bim, Nip3, Nix) cell death (Reed, J. *Oncogene* 17, 3225-3236(1998); Reed, J. C. *Amer J Pathol* 157, 1415-1430(2000)).

Bcl-2 family proteins contain at least one of four conserved regions, termed Bcl-2 Homology (BH) domains. Most members of this family also contain a transmembrane (TM) domain located near the carboxyl-terminus that anchors them in intracellular membranes of mitochondria and other organelles (Reed, J. *Oncogene* 17, 3225-3236(1998); Reed, J. C. *Amer J Pathol* 157, 1415-1430(2000)).

Many Bcl-2 family proteins are capable of physically interacting, forming homo- or hetero-dimers, and functioning as agonists or antagonists of each other (Reed, J. *Oncogene* 17, 3225-3236 (1998); Reed, J. C. *Amer J Pathol* 157, 1415-1430 (2000); Oltvai, Z. N., and Korsmeyer, S. J. *Cell* 79, 189-192 (1994)). Specificity for interaction partners and tissue-specific patterns of expression combine to endow each Bcl-2 protein with a physiological role in vivo, resulting for example in highly diverse phenotypes when members of this multigene family are individually knocked-out in mice (Vaux, D. and Korsmeyer, S. *Cell* 96, 245-254 (1999)).

Thus, a need exists to identify members of the Bcl-2 family and to elucidate their functional characteristics. The present invention we describe the molecular cloning and initial characterization of a new human member of the Bcl-2 family, Bcl-B.

SUMMARY

The present invention is based in part on the identification and characterization of a novel member of the Bcl-2 family of apoptosis modulators, denoted Bcl-B. Bcl-B is capable of modulating apoptosis in cells. For example, Bcl-B inhibits apoptosis induced by Bax. Bcl-B also binds to itself as well as other modulators of apoptosis including, for example, Bax, Bcl-2 and Bcl-XL. Thus, Bcl-B is involved in apoptotic signaling as well as modulating activity or activation of other proteins, or having its own activity modulated by other proteins associated with programmed cell death. Accordingly, compositions of the invention, including, for example, Bcl-B polypeptides, polynucleotides, antibodies and subsequences thereof are useful for modulating apoptosis and associated signaling pathways, as well as for detecting Bcl-B (e.g., for diagnosis or monitoring Bcl-B based therapy) and identifying agents that affect Bcl-B expression, activity or binding.

Thus, in accordance with the invention there are provided isolated and recombinant BCl-B nucleic acids. In one embodiment, a BCl-B nucleic acid includes a polynucleotide sequence having at least about 70% identity to SEQ ID NO:1, wherein the sequence is distinct from EST Accession no. AA098865, which is TCCGCCTACCTCGGCTACCCCGG-GAACCGCTTCGAGCTGGTGGCGCTGATGG CGGAT-TCCGTGCTCTCCGACAGCCCCGGC-CCCACCTGGGAGNAGTGGTGACG CTCGTGACCTTCGCAGGGACGCTGCT (SEQ ID NO: 37). In additional embodiments, a Bcl-B nucleic acid includes a polynucleotide sequence having at least about 80%, 90%, 95% or more identity to SEQ ID NO:1, wherein the sequence is distinct from EST Accession no. AA098865. In still other embodiments, a Bcl-B nucleic acid encodes a polypeptide that modulates apoptosis (e.g., a sequence set forth or including SEQ ID NO:2). Polynucleotide sequences included in the invention can be of any size, for example, a sequence less than about 50 kB, less than about 25 kB, less than about 10 kB, less than about 5 kB, less than about 2.5 kB, or between about 2.5 kB and 1 kB, 1 kB and 0.5 kB, 0.5 kB and 0.25 kB, and 0.1 kB and 15 base pairs.

In additional embodiments, isolated or recombinant nucleic acids include SEQ ID NO:1; SEQ ID NO:1, wherein one or more T's are U; nucleic acid sequences complementary to SEQ ID NO:1 and SEQ ID NO:1, wherein one or more T's are U; and subsequences thereof that are at least 15 base pairs long, e.g., a length of about 12-30, 30-50, 50-100, 100-250, 250-500, 500-1000, 1000-2500, 2500-5000 or 5000-10000 base pairs.

In yet additional embodiments, nucleic acids include sequences that hybridize to a sequence set forth as SEQ ID NO:1, wherein the nucleic acid is distinct from Accession no.

AA098865. In various aspects, the sequences hybridize under low, moderate or stringent hybridization conditions.

Invention nucleic acids can be expressed (e.g., transcribed and/or translated) in solution or solid phase, or in cells tissue or organs in vitro, ex vivo or in vivo. In order to express the Bcl-B polynucleotides, they can be linked to cis-acting nucleic acid sequences, such as promoters, enhancers and other transcription/translation control elements. Thus, the invention further provides expression cassettes including a Bcl-B polynucleotide sequence operably linked to an expression control element. In one embodiment, a polynucleotide sequence operably linked to an expression control element has at least about 70% identity to SEQ ID NO:1. In one aspect, the polynucleotide sequence encodes a polypeptide that inhibits apoptosis or an antisense that stimulates or induces apoptosis (e.g., stimulates or inhibits Bax mediated apoptosis). In another aspect, the polynucleotide sequence encodes a polypeptide comprising SEQ ID NO:2. In other embodiments, the expression cassette includes a promoter or enhancer, for example, a constitutive, inducible, tissue-specific or developmentally regulated promoter or enhancer. In additional embodiments, an expression cassette further comprises a vector. In various aspects, a vector confers expression in bacteria, plant, insect, mammalian or a yeast cell. In additional aspects, a vector comprises a viral vector such as an adenovirus, retrovirus, adenovirus, adeno-associated virus, lentivirus, reovirus, rotavirus, herpes simplex virus, parvovirus, papilloma virus or cytomegalovirus.

The invention also provides isolated and recombinant Bcl-B polypeptides. In one embodiment, an isolated or recombinant polypeptide includes a sequence having at least about 65% identity to SEQ ID NO:2, and having one or more activities of the polypeptide set forth in SEQ ID NO:2. In various aspects, the isolated or recombinant polypeptide has at least about 75%, 85%, 90%, 95% or more identity to SEQ ID NO:2. Polypeptide sequences included in the invention can be of any size, for example, a sequence at least about 15, 20, 25, 30, 40, 50, 75, 125, 150 or 200 or more amino acids in length. Bcl-B polypeptides generally have one or more activities as set forth herein, for example, modulating apoptosis (e.g., inhibits Bax mediated apoptosis) in a cell (e.g., bacteria, plant, insect, mammalian or yeast). In various aspects, the cell is a human cell such as a heart, brain, lung, kidney, liver, pancreas, spleen, thymus, colon, leukocyte, small intestine, testis, prostate or ovarian cell, and optionally expresses bax.

Polypeptide sequences of the invention include modified forms that retain, at least a part of, one or more activities or functions of wild type Bcl-B. Exemplary Bcl-B activities include, for example, modulating apoptosis, homodimerization, heteromerization, binding to Bcl-2, Bcl-XL or Bax, forming a membrane channel, associating with mitochondria, or immunogenicity. In one embodiment, the polypeptide contains a transmembrane domain substantially the same as the underlined amino acid sequence set forth in FIG. 1A (SEQ ID NO:13). In another embodiment, the polypeptide contains one or more BH1, BH2, BH3 or BH4 domains set forth in FIG. 1A.

Polypeptide sequences of the invention include chimeric forms of Bcl-B (e.g., having at least about 65% identity to SEQ ID NO:2, optionally encoded by a polynucleotide sequence having at least about 70% identity to SEQ ID NO:1) and fused to a second polypeptide sequence (e.g., different amino acid sequences). In one embodiment, a second polypeptide sequence comprises a tag. In another embodiment, a Bcl-B polypeptide includes a transmembrane domain of a mitochondrial protein or another Bcl-2 protein family member transmembrane domain.

The invention further provides antibodies that specifically bind to a Bcl-B polypeptide. In one embodiment, an antibody binds to a sequence in or including a sequence set forth in SEQ ID NO:2, for example, an immunogenic subsequence thereof. In other embodiments, the antibody modulates an activity or function of Bcl-B. Exemplary Bcl-B activities modulated by an antibody include, for example, one or more of modulating apoptosis, homodimerization, heteromerization, binding to Bcl-2, Bcl-XL or Bax, forming a membrane channel, associating with mitochondria, or immunogenicity.

Invention nucleic acids, polypeptides, antibodies and other compositions set forth herein may be attached to a substrate. Thus, the invention provides substrates that include Bcl-B nucleic acids, polypeptides and antibodies suitable for detection, genetic or expression profiling or diagnosis. For example, in one embodiment, a Bcl-B nucleic acid, polypeptide or antibody is attached to a two-dimensional detection substrate in which a plurality of other molecules are attached at discrete defined positions (i.e., addresses).

Invention nucleic acids, polypeptides, antibodies and other compositions set forth herein may be expressed in cells, in vitro, ex vivo or in vivo. Thus, the invention provides transformed cells including a Bcl-B nucleic acid, polypeptide or antibody. In various aspects, the cell is a bacteria, plant, insect, mammalian (e.g., human) or yeast cell.

Invention nucleic acids, polypeptides, antibodies and other compositions set forth herein may be expressed in animals, including non-human transgenic animals. In one embodiment, a non-human transgenic animal includes a polynucleotide sequence having at least about 70% identity to SEQ ID NO:1. In another embodiment, a non-human transgenic animal expresses a polypeptide or an antisense that modulates apoptosis. In yet another embodiment, expression of the polypeptide or antisense is tissue-specific or is in one or more cells of a non-human transgenic animal (e.g., in one or more of heart, brain, lung, kidney, liver, pancreas, spleen, thymus, colon, muscle, leukocyte, small intestine, testis, prostate or ovary). Transgenic animals include progeny thereof, homozygous or heterozygous in respect to the Bcl-B molecule.

Invention nucleic acids, polypeptides, antibodies and other compositions set forth herein may be expressed in plants. The invention therefore provides plants, plant parts and seeds that can express Bcl-B nucleic acids, polypeptides and antibodies. In one embodiment, a transgenic plant, plant part or seed includes a nucleic acid sequence having at least about 70% identity to SEQ ID NO:1. In another embodiment, a transgenic plant, plant part or seed includes a nucleic acid encoding a polypeptide that modulates apoptosis. In one aspect, at least a portion of the plant exhibits a decreased level of senescence. In yet another embodiment, a transgenic plant, plant part or seed is resistant to abiotic insult, such as an insult induced by high moisture, low moisture, salinity, nutrient deficiency, air pollution, high temperature, low temperature, soil toxicity, herbicide or insecticide, or biotic insult, such as an insult induced by a plant pathogen (e.g., a virus, fungus, bacteria or nematode.

Invention nucleic acids, polypeptides, antibodies, including cells, plants, substrates, transgenic animals and other compositions set forth herein may be included in kits. Thus, the invention provides kits including, inter alia, Bcl-B nucleic acids, polypeptides, antibodies, including cells, plants, substrates and transgenic animals in a container. In various embodiments, a kit includes instructions suitable for using one or more of the kit components. In one aspect, instructions are for detecting a polynucleotide sequence having at least about 70% identity to SEQ ID NO:1, a polynucleotide or polypeptide that binds to a polypeptide of claim 46, or a polypeptide in or including a sequence set forth in SEQ ID NO:2.

Invention nucleic acids, polypeptides, antibodies, including cells, may be included in pharmaceutical formulations. Thus, the invention additionally provides isolated or recombinant Bcl-B nucleic acids, polypeptides, antibodies and cells in a pharmaceutically acceptable carrier. Pharmaceutical carriers include those suitable for particular routes of administration including, for example, intracranial, intravenous, intramuscular, subcutaneous, via intubation, inhalation, oral, topical (ocular or nasal), or intra-cavity (rectal or vaginal).

The invention furthermore provides methods of producing Bcl-B nucleic acids, polypeptides, antibodies, including substrates, cells, plants, transgenic animals and other compositions set forth herein. In one embodiment, a method of producing a Bcl-B polypeptide includes expressing a nucleic acid encoding an amino acid sequence having at least about 65% identity to SEQ ID NO:2 in solution, in solid phase, or in a cell in vitro or in vivo.

The invention moreover provides methods for detecting Bcl-B nucleic acids and polypeptides, including cells, plants, transgenic animals and other compositions containing Bcl-B set forth herein. In one embodiment, a method for detecting the presence of a polynucleotide sequence encoding a Bcl-B amino acid sequence having at least about 65% identity to SEQ ID NO:2, or an encoded Bcl-B polypeptide, includes: contacting a sample with a polynucleotide sequence having at least about 70% identity to SEQ ID NO:1 or a Bcl-B antibody; and detecting the presence of a polynucleotide sequence encoding an amino acid sequence having at least about 65% identity to SEQ ID NO:2, or a Bcl-B polypeptide in the sample. Invention compositions including Bcl-B nucleic acids (sense and antisense), polypeptides and antibodies are useful for modulating apoptosis of cells in vitro, in vivo and ex vivo. Thus, the invention provides methods for modulating apoptosis of cells, in vitro, in vivo and ex vivo, optionally in a subject, such as a mammalian (e.g., human) subject. In one embodiment, a method for modulating apoptosis includes contacting a cell with a Bcl-B polypeptide, a polynucleotide sequence having at least about 70% identity to SEQ ID NO:1 or an antisense thereof, or a Bcl-B antibody in an amount sufficient to modulate apoptosis in the cell. In one aspect, the antisense comprises a sequence complementary to Bcl-B sense strand, a sequence that forms a triplex with Bcl-B, a ribozyme, a DNAzyme or an RNAi molecule. In another aspect, apoptosis is induced or increased. In another aspect, apoptosis is prevented or inhibited. In yet another aspect, the cell is at risk of apoptosis or is undergoing apoptosis. In a further aspect, the cell is or is at risk of undesirable proliferation or is undergoing hyperproliferation. In still another aspect, the cell expresses Bax. Exemplary cells in which apoptosis can be modulated include, for example, heart, brain, lung, kidney, liver, pancreas, spleen, thymus, colon, leukocyte, small intestine, testis, prostate and ovarian cells.

Methods of the invention further include modulating apoptosis in a subject. In one embodiment, a method includes administering to the subject an amount of a Bcl-B polypeptide, a polynucleotide sequence having at least about 70% identity to SEQ ID NO:1 or an antisense thereof, or a Bcl-B antibody sufficient to modulate apoptosis in the subject. Candidate subjects having or at risk of a disorder or pathological condition associated with apoptosis may be treated. Thus in another embodiment, a method includes administering to a subject having or at risk of a disorder associated with apoptosis with an amount of a Bcl-B polypeptide, a polynucleotide sequence having at least about 70% identity to SEQ ID NO:1 or an antisense thereof, or a Bcl-B antibody sufficient to treat the subject having or at risk of a disorder associated with apoptosis.

In one aspect, the antisense comprises a sequence complementary to Bcl-B sense strand, a sequence that forms a triplex with Bcl-B, a ribozyme, a DNAzyme or an RNAi molecule.

Subjects suffering or at risk of suffering from a disorder associated with apoptosis include those having a cell degenerative or proliferative disorders. Thus, disorders treatable in a method of the invention include, for example, a neoplasia, autoimmune disorder or fibrotic condition. In particular aspects, the disorder is characterized by neural or muscle degeneration, such as Alzheimer's disease, Parkinson's disease, Creutzfeldt-Jacob's disease (CJD), Huntington disease (HD), Machado-Joseph disease (MJD), Spinocerebellar ataxias 1, 2 and 6 (SCA-1, -2 and -6), dentatorubropallidoluysian atrophy (DRPLA), Kennedy's disease, ischemia, stroke and head trauma, for example. In additional particular aspects, apoptosis or the disorder associated with apoptosis is present in one or more cells of heart, brain, lung, kidney, liver, pancreas, spleen, thymus, colon, muscle, leukocyte, small intestine, testis, prostate or ovary.

Invention compositions are useful as reagents. For example, as Bcl-B modulates apoptosis, genes or agents or molecules that modulate Bcl-B expression, activity or function, for example, promote or inhibit Bcl-B expression or Bcl-B binding with bax, in turn modulate apoptosis. Thus, the invention also provides methods for identifying a gene or agent or molecule in solution, in solid phase, or in a cell that modulates expression or activity of a Bcl-B polypeptide. In one embodiment, a method includes: contacting a cell that expresses Bcl-B polypeptide with a test gene or test agent; and measuring expression or activity of Bcl-B or nucleic acid encoding Bcl-B polypeptide, wherein an increase or decrease in the amount of Bcl-B polypeptide or nucleic acid encoding Bcl-B polypeptide or activity of Bcl-B polypeptide identifies the test gene or test agent as a modulator of Bcl-B polypeptide's expression or activity. In another embodiment, a method includes contacting Bcl-B with a test agent and identifying an agent (e.g., polypeptide) that binds to Bcl-B. In one aspect, Bcl-B polypeptide contains one or more 15N-labeled amino acids, and binding is detected by resonance changes in Bcl-B polypeptide. In another aspect, the test agent (i.e., molecule) comprises a polypeptide sequence (e.g., an antibody). In yet another aspect, the test agent is attached to the surface of a substrate. As set forth herein, test agents include libraries of molecules. Test agents may be attached at discrete positions of a substrate. The binding agent identified can subsequently be tested for modulating one or more activities or functions of Bcl-B.

In yet another embodiment, a method includes contacting Bcl-B with a binding molecule (e.g., Bax, Bcl-B, or a Bcl-2 protein family member such as Bcl-2 or Bcl-XL) under conditions allowing binding in the presence and absence of a test agent; and measuring binding between Bcl-B and the molecule (e.g., Bax, Bcl-B, or a Bcl-2 protein family member such as Bcl-2 or Bcl-XL) in the presence and absence of the test agent; increased or decreased binding identifies an agent that modulates binding of Bcl-B to the binding molecule. In various aspects, the method is performed in solution, solid phase or in a cell, in vitro or in vivo, for example, in a bacteria, plant, insect, mammalian or yeast cell. In another aspect, a the assay comprises a two-hybrid system for expressing Bcl-B and the binding molecule. In another aspect, in vitro binding is measured by detecting fluorescence of Bcl-B conjugated to a fluorophore.

Bcl-B activities or functions that may be measured in order to practice one or more methods of the invention include, for example, increased or decreased cell apoptosis, DNA fragmentation or caspase activity, cell survival, proliferation, differentiation, or Bcl-B binding to Bax, Bcl-B, Bcl-2 or Bcl-XL. Such methods can be performed in solid phase, solution, in vitro or in vivo. In various aspects, a method is performed in a cell, such as a bacteria, plant, insect, mammalian or yeast cell. Cells used in the methods need not naturally express Bcl-B. Thus, in another aspect, the cell has been transformed with a nucleic acid that encodes Bcl-B. Test genes or test agents include libraries of genes or agents.

In additional embodiments, a method for identifying an agent that modulates activity of a Bcl-B polypeptide includes: contacting a membrane channel created with Bcl-B under conditions allowing transport of a molecule through the membrane channel with a test agent; and measuring transport of the molecule in the presence of the test agent in comparison to transport in the absence of the test agent, wherein increased or decreased transport of the molecule in the presence of the test agent identifies an agent that modulates activity of a Bcl-B polypeptide. In one aspect, a Bcl-B polypeptide comprises a BH4 domain. In another aspect, the membrane is synthetic or natural. In yet another aspect, the molecule comprises an ion.

Invention reagents are also useful for detecting Bcl-B nucleic acid, protein and antibody. Thus, the invention provides methods of detecting Bcl-B nucleic acid, protein and antibody in a sample, in solution, in solid phase, in a cell or in situ. In one embodiment, a method includes: contacting a sample having or suspected of having Bcl-B protein or nucleic acid encoding Bcl-B with a Bcl-B antibody or nucleic acid having at least about 70% identity to SEQ ID NO:1 under conditions allowing binding; separating bound protein or nucleic acid from unbound protein or nucleic acid; and determining the amount of Bcl-B protein or nucleic acid having about 70% identity to SEQ ID NO:1 thereby detecting Bcl-B protein or nucleic acid encoding Bcl-B in the sample. Samples may be from a subject, in which case they may detect abnormal amounts of Bcl-B which in turn indicates a disorder associated with apoptosis. Thus, in various aspects, the sample is obtained from a subject having or at risk of having a cell proliferative (e.g., hyperproliferation) or degenerative disorder (e.g., undesirable apoptosis).

DETAILED DESCRIPTION

Figure 1:
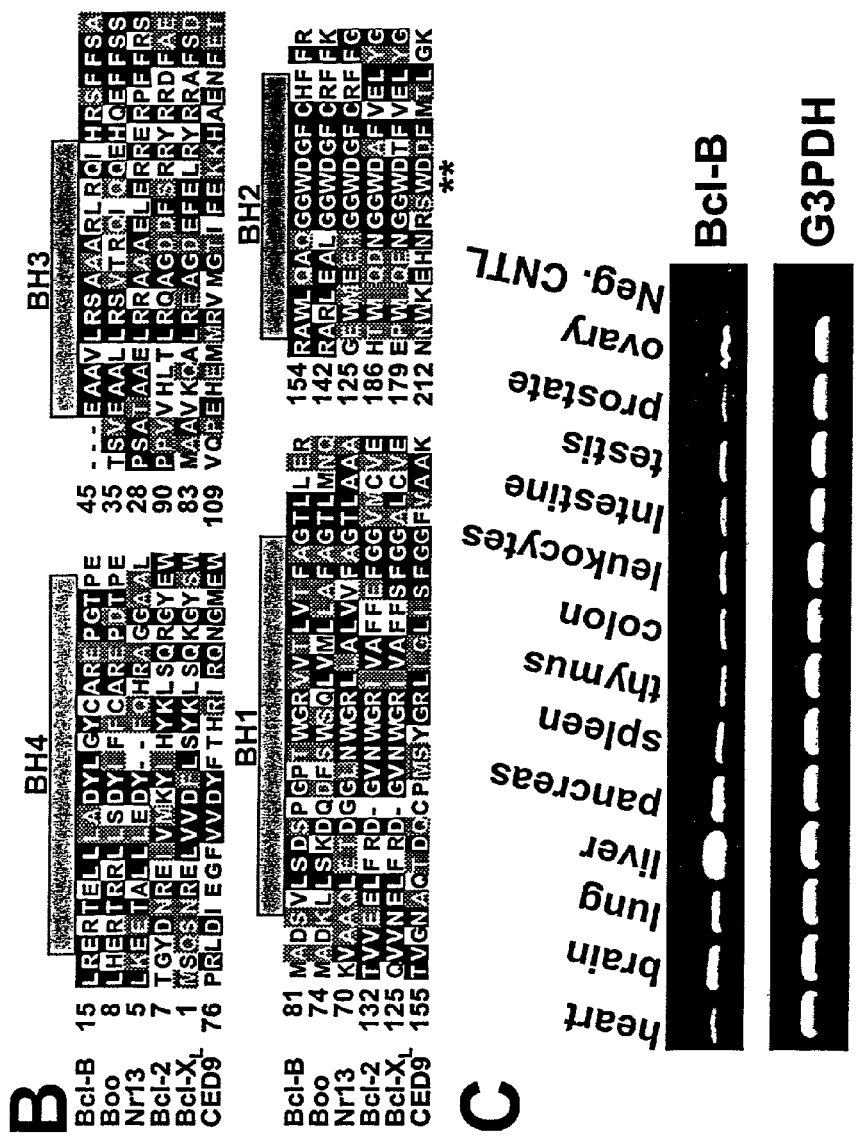
FIG. 1 shows (A) The predicted amino-acid sequence of exemplary Bcl-B (SEQ ID NO:2); the transmembrane domain (TM) is underlined. (B) An alignment of Bcl-B BH1, BH2, BH3 and BH4 domains with other Bcl-2 family proteins (SEQ ID NOs:13-36). Numbers on the left indicate the position of the amino-acid in each protein based on Genbank AAD08703 (murine Boo), Q90343 (chicken Nr13), AAA35591 (hu Bcl-2), CAA80661 (hu Bcl-XL), and P41958 (*C. elegans* CED9); black and gray boxes indicate identical and similar residues, respectively; asterisks under the BH2 alignment indicate the intron junction for hu BCL-B, BCL-2, and BCL-X genes. (C) Expression of BCL-B in adult human tissues.

The invention provides polypeptides that "modulate apoptosis," proteins that increase or induce apoptosis or decrease or prevent programmed cell death, including exemplary Bcl-B (FIG. 1A, e.g., SEQ ID NO:2). The invention also provides nucleic acids encoding polypeptides that "modulate apoptosis," including exemplary Bcl-B (Example 2, e.g., SEQ ID NO:1). The invention further provides antibodies that bind to Bcl-B including antibodies that increase an activity of Bcl-B (i.e., an agonistic antibody) and antibodies that decrease an activity of Bcl-B (i.e., an antagonistic antibody). Also provided are polynucleotides (e.g., oligonucleotide probes) of various lengths that hybridize to Bcl-B set forth in SEQ ID NO:1. Methods for making these compositions are also provided. Kits containing invention compositions in a container, including instructions for use (e.g., written on a hard copy or a computer readable medium), for example, for modulating apoptosis, for detecting Bcl-B activity, expression or binding, or identifying an agent that modulates Bcl-B activity, expression or binding are provided.

Invention compositions have various activities including the ability to modulate apoptosis. Thus, invention compositions are useful as therapeutic agents for increasing or decreasing apoptosis. For example, Bcl-B protein, having wild type function or dominant negative activity, can be expressed in a cell, tissue or organ in order to modulate apoptosis. Antisense and antisense like molecules such as ribozymes, DNAzymes or RNAi (RNA interference) molecules (collectively referred to herein as "antisense") that inhibit expression of Bcl-B can reduce the level of Bcl-B gene expression, thus reducing the level of Bcl-B activity. Accordingly, the compositions can be used to manipulate apoptotic ("cell death") mechanisms in a variety of cell types, including insect, plant and mammalian, such as human, cells, and organisms. The invention therefore provides methods for increasing or decreasing apoptosis in a cell, tissue or organ in vitro, ex vivo or in vivo (e.g., in a subject in need of increased or decreased apoptosis).

Invention compositions also are useful as diagnostic markers. In particular, Bcl-B modulates apoptosis and, therefore, may indicate normal or altered apoptosis. For example, greater than normal levels of Bcl-B in a cell, tissue or organ may characterize the cell, tissue or organ as proliferative or hyperproliferative. In contrast, less than normal levels of Bcl-B in a cell, tissue or organ B may characterize the cell, tissue or organ as slowly proliferating, non-proliferating, at risk of apoptosis or undergoing apoptosis. Thus, detecting Bcl-B (nucleic acid or protein) or Bcl-B activity or expression can be used to as a diagnostic marker. Detecting Bcl-B activity or expression may also be useful for assessing a subject's risk of developing altered apoptosis or indicate a prognosis for a condition or disorder associated with apoptosis.

Bcl-B compositions are also useful for identifying agents, including therapeutic agents for treating disorders associated with apoptosis. In a method of the invention, Bcl-B (protein or nucleic acid) is contacted with a test agent and binding of Bcl-B to the agent is determined. Binding of Bcl-B to binding molecules (e.g., Bax, Bcl-2 or Bcl-$X_L$) in the presence of a test agent can be used to identify agents that inhibit or promote Bcl-B binding to a binding molecule in another method of the invention, Bcl-B activity or expression is determined in the presence of a test agent in order to identify agents that modulate Bcl-B activity or expression. Agents that modulate Bcl-B activity, expression or binding to a binding molecule are useful for modulating apoptosis. Agents that bind Bcl-B may also be useful as markers to indicate the presence of Bcl-B.

Additional invention methods are based on other Bcl-B activities, such as the ability of Bcl-B to bind to cellular molecules associated with apoptosis. Invention compositions are therefore also useful as therapeutic targets. For example, in a method of the invention, contacting Bcl-B with a molecule that binds Bcl-B, for example, contacting Bcl-B with Bax, Bcl-2 or Bcl-$X_L$ can be used to modulate a Bcl-B activity, such as apoptosis (increasing or decreasing). Bcl-B can also be targeted with agents that modulate Bcl-B activity or expression (e.g., antisense or ribozymes or DNAzymes or RNAi), or Bcl-B binding to binding molecules.

Modulating apoptosis in cells with invention compositions allows treatment of physiological conditions associated with undesirable or insufficient apoptosis, or undesirable cell survival, growth or proliferation (e.g., where apoptosis is less than normal or desired), ex vivo or in vivo in a subject. Conditions associated with undesirable apoptosis/cell death or undesirable cell survival/growth/proliferation include cell degenerative and proliferative disorders. Organ and organ systems affected by degenerative disorders include, for example, the nervous system (brain, spinal cord, neurons associated with tissues and organs) skeletal-muscular system (voluntary muscles) and the cardio-respiratory system (heart and blood vessels). Specific examples of neurodegeneration include cell death caused by stroke and head trauma, Alzheimer's disease, Parkinson's disease, Creutzfeldt-Jacob's disease (CJD), Huntington disease (HD), Machado-Joseph disease (MJD), ataxias (Spinocerebellar ataxias 1, 2 and 6; SCA-1, -2 and -6), dentatorubropallidoluysian atrophy (DRPLA) and Kennedy's disease. Specific examples of muscle degeneration include muscular dystrophy. Specific examples of cardiac degeneration include ischemia caused by heart trauma e.g., associated with or resulting from a heart attack, or insufficient blood supply, or oxygen. Such disorders are but a few of the specific examples of disorders treatable with a method of the invention.

Apoptotic disorders are caused by various molecular mechanisms. For example, particular amino acid sequences are known to confer apoptosis, such as polyglutamine repeat sequences (polyGln) and protein sequences within cell receptors, such as the neurotrophin receptor. Caspases are also known to mediate the apoptotic signaling pathway in cells. Thus, conditions treatable with the compositions of the invention include cells, tissue and organs in which such apoptosis inducing or increasing proteins are expressed or active.

Bcl-B was initially identified using a genetic screen of a human liver library. A TBLASTN search of the human Expressed Sequence Tag (EST) database using the amino-acid sequence of the mouse Boo/Diva as a query identified partial cDNA having homology with Boo. A human EST clone (Accession No. AA098865) which is TCCGCCTAC-CTCGGCTACCCCGGGAACCGCTTC-GAGCTGGTGGCGCTGATGG CGGATTCCGTGCTCTC-CGACAGCCCCGGCCCCACCTGGGAGNAGTGGTGACG CTCGTGACCTTCGCAGGGACGCTGCT (SEQ ID NO: 37), was obtained and sequenced in its entirety, revealing an open reading frame (ORF) encompassing the last 151 residues of a protein with homology to Boo (Bcl-B).

Structurally, Bcl-B is characterized as having four "BH" domains, denoted BH1, BH2, BH3 and BH4. The sequences of the domains for exemplary Bcl-B are BH1, VLSD-SPGPTWGRVVTLVTFAG; BH2, AWLQAQGGWDG-FCHF; BH3, EAAVLRSAAARLRQI; and BH4, ERTELLLADYLGYCAREPGTP (SEQ ID NOS: 3-6, respectively). These domains are present in other Bcl-2 family member proteins that inhibit apoptosis. Comparisons of this predicted sequence with all known Bcl-2 family members by BLAST search indicated that it is most similar to the murine Bcl-2-family protein Boo (also known as Diva). Exemplary Bcl-B (SEQ ID NO:2) shares 47% amino-acid sequence identity with Boo.

The BCL-B gene is comprised of two exons interrupted by a ~2.3 kbp intron. The location of this intron corresponds precisely to the intronic interruption in the coding region of the anti-apoptotic BCL-2 and BCL-X genes (corresponding to the motif GGW^D in BH2). By comparison to BCL-B, the pro-apoptotic genes BAX and BAK have more complicated exon-intron organizations, in which the coding regions of the gene are spread over 5 (Bak) or 6 (Bax) exons. The similar genomic organization of the BCL-2, BCL-XL, and BCL-B genes thus suggests they evolved from a common ancestor and indirectly implies a similar mechanism of action for their encoded proteins.

In transfection assays performed in four different human tumor cell lines, anti-apoptotic activity of Bcl-B was observed. Bcl-B binds and suppresses apoptosis-induction by Bax, but does not detectably interact with Bak or modulate apoptosis induced by Bak over-expression. However, because Bcl-B is capable of associating with either anti-apoptotic proteins (e.g., Bcl-2 and Bcl-$X_L$) or with the pro-apoptotic proteins (e.g., Bax), it is possible that Bcl-B displays different effects on apoptosis, cell proliferation, survival, growth or differentiation depending on cellular context. A similar phenomenon has been reported for some other Bcl-2 family proteins. For example, Bcl-2 reportedly promotes apoptosis in photoreceptor cells of the retina while Bax can suppress cell death in some types of neurons (Chen et al., *Proc. Natl. Acad. Sci. USA* 93, 7042-7047 (1996); Middleton et al., *Development* 122, 695-701 (1996)). Thus, Bcl-B is likely to inhibit cell apoptosis, proliferation, survival, growth or differentiation, in some cellular contexts and promote cell apoptosis proliferation, survival, growth or differentiation in other cellular contexts.

The Bcl-B transmembrane (TM) domain is important for apoptosis-inhibiting activity, as well as for intracellular localization to mitochondria. Deletion of the domain reduces Bcl-B ability to inhibit apoptosis as well as reduces association with mitochondria. Replacing the native Bcl-B transmembrane domain with other transmembrane domains, including those targeting mitochondria, will likely restore Bcl-B apoptosis modulating activity. Thus, the invention includes Bcl-B polypeptides and subsequences having non-Bcl-B transmembrane domains, for example, from Bcl-2, Bax, Bak, Bcl-$X_L$, etc.

The correlation between membrane-targeting and function is reminiscent of some other Bcl-2 family proteins indicating that the site of action of Bcl-B is close to the intracellular organelles, including mitochondria, with which it associates. Though roughly half the Bcl-BΔTM protein was associated with the HM membrane fraction in cells, this may be due to its dimerization with other resident Bcl-2 family proteins. A membrane site of action for Bcl-B would be consistent with evidence that several Bcl-2 family proteins are capable of forming ion channels or pores in membranes. Indeed, molecular modeling of Bcl-B on the structure of Bcl-$X_L$ suggests that it possesses a similar overall fold and that it contains amphipathic α-helices similar to the putative pore-forming α5 and α6 of Bcl-$X_L$.

The differences observed in the activity and protein interaction partners of murine Boo and human Bcl-B proteins indicate that Bcl-B does not represent the human orthologue of mouse Boo/Diva. Also consistent with this interpretation is the difference in the expression patterns of Bcl-B and Boo. For example, although Boo (Diva) is expressed predominantly in ovary, testis, and epididymis in adult mice, Bcl-B mRNA is widely expressed in adult human tissues.

Weak interactions of Bcl-B with Apaf1 in co-immunoprecipitation assays have been detected but functional analysis has yet to reveal an effect of Bcl-B on Apaf1-induced apoptosis. Since Apaf1 is a soluble cytosolic protein, the inability of Bcl-BΔTM to suppress Bax-induced apoptosis suggests that Bcl-B may not play a significant role in suppressing Apaf1. Moreover, the observation that Bcl-B suppresses apoptosis induced by Bax but not Bak also argues against a role for Bcl-B as an Apaf1 suppresser, given that both Bax and Bak induce mitochondrial release of the Apaf1-activator, cytochrome c. However, though Bcl-B may not regulate Apaf1, it is possible that it binds to and suppresses the activity of some other unidentified Apaf1-like, CED4-family protein, analogous to CED9, with which Bcl-B shares 20% amino-acid sequence identity (53% similarity).

As used herein, the term "apoptosis" or "programmed cell death" means that the cell (tissue or organ) exhibits one or more characteristics associated with programmed cell death. Characteristics include inhibition of cell survival, growth, death or differentiation, protein/nucleic acid cleavage/fragmentation, chromatin condensation, membrane fragmentation, changes in expression or activity of one or more proteins that promote apoptosis or that inhibit apoptosis, for example, increased caspase (e.g., caspase-3, -7 or -9) or Fas activity or expression, increased expression of proteins containing amplified polyglutamine repeat sequences or amplification of the sequences themselves, protein aggregate formation, etc. "Modulating" apoptosis means increasing, stimulating or inducing, or decreasing, inhibiting, blocking or preventing (e.g., prophylaxis) one or more characteristics of programmed cell death as described herein or known in the art. As described herein, compositions of the invention, including Bcl-B polypeptides, antibodies and subsequences thereof and antisense can have one or more apoptosis modulating activities.

As used herein, the term "isolated," when referring to a molecule or composition, such as a nucleic acid, polypeptide or antibody of the invention, means that the molecule or composition is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. Components naturally associated with nucleic acid and protein include cellular components such as membrane, sugars, carbohydrate, lipids, fats, small molecules (e.g., hormones), etc.

As used herein, "recombinant" refers to a polynucleotide synthesized or otherwise manipulated in vitro (e.g., "recombinant polynucleotide"), to methods of using recombinant polynucleotides to produce gene products in vitro, in cells or in other biological systems, or to a polypeptide ("recombinant protein") encoded by a recombinant polynucleotide.

A composition of the invention can also be "substantially pure." For example, a substantially pure Bcl-B protein will generally be free (30% or less measured by mass) of contaminating cellular components. A substantially pure composition can be free from chemical precursors or other chemicals when chemically synthesized, such as chemical intermediates or byproducts used to synthesize proteins or nucleic acids or that are byproducts of such chemical synthesis procedures. Thus, "substantially pure" can mean Bcl-B protein having less than about 30%, 20%, 10% and more likely 5% (by dry weight), of non-Bcl-B protein (also referred to herein as a "contaminating protein"), of chemical precursors, or of culture medium, i.e., culture medium is less than about 30% of the volume of the protein preparation. An isolated composition can therefore be in a homogeneous state. It can be in a dry or an aqueous solution. The invention includes isolated or purified preparations (protein or nucleic acid) of at least 0.01, 0.1, 1.0, and 10 milligrams in dry weight. Purity and homogeneity can be determined, e.g., using analytical chemistry techniques such as, e.g., polyacrylamide gel electrophoresis (SDS-PAGE) or high performance liquid chromatography (HPLC).

The terms "nucleic acid," "nucleic acid sequence" or "polynucleotide" are used interchangeably to refer to a deoxy-ribonucleotide or ribonucleotide oligonucleotide, including single- or double-stranded forms, and coding or non-coding (e.g., "antisense") forms. Antisense includes single strand non-coding sequence complementary to coding sequence (i.e. sense strand), triplex forming sequences as well as single and double strand ribozymes, DNAzymes and RNAi.

The term encompasses nucleic acids containing analogues of natural nucleotides. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532, 226; Samstag (1996) Antisense Nucleic Acid Drug Dev 6:153-156).

The term nucleic acid is used interchangeably with gene, DNA, RNA, cDNA, mRNA, oligonucleotide primer, probe and amplification product. Nucleic acid molecules encoding Bcl-B polypeptides, proteins or amino acid sequences, hybridize to Bcl-B encoding nucleic acids or have the recited percent identity to Bcl-B set forth in SEQ ID NO:1 are collectively referred to as "nucleic acids or polynucleotides of the invention" or "Bcl-B nucleic acids or polynucleotides."

The term "heterologous" when used in reference to a nucleic acid, indicates that the nucleic acid is in a cell or plant where it is not normally found in nature; or, comprises two or more nucleic acid subsequences which are not found in the same relationship to each other as normally found in nature, or is recombinantly engineered so that its level of expression, or physical relationship to other nucleic acids or other molecules in a cell, or structure, is not normally found in nature. For example, a heterologous nucleic acid is typically recombinantly produced, having two or more sequences from unrelated genes, such as a recombinant chimeric protein having one or more amino acids from different proteins, arranged in a manner not found in nature; e.g., a promoter sequence operably linked to a nucleic of the invention. As another example, the invention provides recombinant constructs (expression cassettes, vectors, viruses, and the like) comprising various combinations of promoters and sequences of the invention.

As used herein the terms "polypeptide," "protein," and "peptide" are used interchangeably and include compositions of the invention such as Bcl-B protein and antibodies that bind Bcl-B, as well as subsequences thereof. Amino acids comprise the polypeptides, all L- or D-isomers, or mixtures thereof. Amino acids also include circularized forms, such as formed by intra- or intermolecular disulfide bonds, or end-to-end amino-carboxyl linkages.

Also included are "analogs," or "conservative variants" and "mimetics" (e.g., "peptidomimetics") with structures and activity that substantially correspond to the polypeptides of the invention, including the exemplary Bcl-B sequence as set forth in SEQ ID NO:2. Thus, the terms "conservative variant" or "analog" or "mimetic" also refer to a polypeptide or peptide which has a modified amino acid sequence, such that the change(s) do not substantially alter the polypeptide's (the conservative variant's) structure and/or activity (e.g., to modulate apoptosis, bind to a binding molecule, etc.), as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity, i.e., they are "substantially the same" in terms of structure or function as an unmodified sequence.

Conservative substitution tables describing chemically and structurally similar amino acids are well known in the art. For example, an exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W. H. Freeman and Company; Schulz and Schirmer (1979) Principles of Protein Structure, Springer-Verlag). One of skill in the art will appreciate that the above-described substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids within an encoded sequence are also considered "conservatively modified variations."

A "non-essential" amino acid is a residue that can be altered from the wild-type sequence of Bcl-B (e.g., the sequence of SEQ ID NO:2) without destroying or, without substantially altering a biological activity. An "essential" amino acid is defined as one which when substituted with a non-conservative amino acid or deleted results in significant loss or complete abolition of activity. For example, amino acid residues that are likely to be essential among the polypeptides of the present invention include, for example, amino acids present in one or more of the BH1, BH2, BH3 and BH4 domains. Essential amino acids are unamenable to non-conservative substitution or deletion of more than a few amino acids (e.g., 1-3 amino acids).

The terms "mimetic" and "peptidomimetic" refer to a synthetic chemical compound that has substantially the same structural or functional characteristics of the polypeptides of the invention (e.g., ability to modulate apoptosis, bind to Bax, Bcl-2 or Bcl-$X_L$, associate with mitochondria, form membrane channels, etc.). The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetics' structure or activity. As with polypeptides of the invention which are conservative variants, routine tests can be used to determine whether a mimetic is within the scope of the invention, i.e., that its function is not substantially altered, e.g., it retains at least part of an activity of native Bcl-B set forth in SEQ ID NO:2. Polypeptide mimetics can contain any combination of natural and non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, etc. A polypeptide can be characterized as a mimetic when one or more of its residues are joined by chemical means other than natural peptide (amide) bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond")

linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

"Expression control elements" are generally cis-acting nucleic acid transcriptional regulatory sequences. Examples include promoters capable of directing expression of a nucleic acid to cells (bacteria, plant, insect, mammalian, yeast, etc.). Examples also include enhancers capable of influencing transcription of a transcribed gene when located at a significant distance from the initiation site, or at the 5', 3' ends, or in an intron within the coding sequence. Expression control elements may contain only the minimum elements needed for transcription of the recombinant nucleic acid, such as a minimal promoter sequence.

An expression control element can be "constitutive," such that transcription of an operably linked nucleic acid occurs without the presence of a signal or stimuli. Expression control elements can confer expression in a manner that is "regulatable," that is, a signal or stimuli (external or internal or produced by other cells, such as a hormone produced by one cell that affects gene expression in another cell) that increases or decreases expression of the operably linked nucleic acid. A regulatable element that increases expression of the operably linked nucleic acid in response to a signal or stimuli is also referred to as an "inducible element" (i.e., is induced by a signal, e.g., a hormone). A regulatable element that decreases expression of the operably linked nucleic acid in response to a signal or stimuli is referred to as a "repressible element" (i.e., the signal decreases expression such that when the signal is removed or absent expression increases). Generally, the amount of increase or decrease conferred by such elements is proportional to the amount of signal or stimuli present. Thus, in the case of an inducible element, the greater an amount of signal or stimuli present the greater the increase in expression. Typically, basal levels of transcription are greater for a repressible element than for an inducible element.

Expression control elements and promoters include those active in a particular tissue or cell type, referred to herein as a "tissue-specific expression control elements." Tissue-specific expression control elements are typically active in specific cell or tissue as they are recognized by transcriptional activator proteins, or other regulators of transcription unique to the specific cell or tissue type. Expression control elements also include elements that confer expression at a particular stage of the cell cycle or differentiation. Accordingly, the invention includes expression control elements that confer constitutive, regulatable, tissue-specific, cell cycle specific, and differentiation stage specific expression.

Expression control elements include other components that influence expression (transcription, translation, RNA or protein stability, etc.), and therefore, include components in addition to promoter and enhancer sequences. Such components include, for example, leader sequences and fusion partner sequences, internal ribosome binding sites (IRES) elements for the creation of multigene, or polycistronic, messages, splice signal for introns, maintenance of the correct reading frame of the gene to permit in-frame translation of mRNA, polyadenylation signal for polyadenylation of the transcript of a gene of interest, stop codons, etc. Thus, a combination of expression control elements might include a cis-acting transcriptional control element promoter, an enhancer, transcription terminator, an origin of replication, a chromosomal integration sequence, 5' and 3' untranslated regions, and an intron. Expression control elements included herein can be from bacteria, yeast, plant, insect or animal (mammalian or non-mammalian), so long as they function to control expression of an operably linked nucleic acid.

The term "expression cassette" refers to any recombinant expression system for expressing a nucleic acid sequence of the invention in vitro or in vivo, constitutively or inducibly, in any cell or organism, including, in addition to insect and plant cells, prokaryotic, yeast, fungal or mammalian (e.g., human) cells. The term includes linear or circular expression systems. The term includes all vectors. The cassettes, when present in a host cell can be episomal, that is maintained apart from the host's genome, or integrate into the genome. Expression cassettes having the ability to self-replicate or not, i.e., drive only transient expression in a cell, are also included. Introduction of expression constructs into target cells can be carried out by conventional methods well known in the art (osmotic shock (e.g., calcium phosphate), electroporation, viral vectors, vesicles or lipid carriers (e.g., lipofection), direct microinjection, etc.

The term "operable linkage," "operably linked" and grammatical variations thereof means that the element or elements referred to are in a physical or functional relation that allows them to function in their intended manner. Thus, for an expression control element such as a promoter to be in operable linkage with a gene, the promoter modulates expression of the gene (increasing or decreasing expression, as appropriate). Likewise, enhancers operably linked to a gene influence expression of the gene, which include sequences located 5' and 3' of the initiation site and in introns, for example. Thus, nucleic acid relatively close to a gene, within a gene and flanking a gene, e.g., within about 1-10, 10-50, 50-100, 100-500, 500-1000 or more nucleotides from the 5' or 3' termini are included. The invention therefore provides nucleic acids of the invention "operably linked" to an expression control element.

Another example of two elements in operable linkage is where expression of a gene influences expression of another gene. For example, a promoter driving expression of a gene encoding a transcription factor which binds to a promoter that activates expression of a second gene is operably linked to the second gene. Similarly, a Bcl-B polypeptide that binds to Bax is operably linked with a protein (or for that matter signaling pathway) influenced by Bax, through binding, or where, for example, Bax regulates transcription of a gene product. The terms operable linkage, operably linked and the like are therefore functionally defined.

The term "vector" refers to nucleic acid, such as a plasmid, virus (e.g., viral vector), or other vehicle known in the art that can be manipulated by insertion or incorporation of a polynucleotide, for genetic manipulation (i.e., "cloning vectors"), or can be used to transcribe or translate the inserted polynucleotide (i.e., "expression vectors"). Such vectors are useful for manipulation of nucleic acids of the invention, for producing invention polypeptides (e.g., baculovirus system), for introducing them into cells or whole organisms (ex vivo or in vivo), and expressing the transcribed Bcl-B antisense or encoded Bcl-B protein in cells in vitro or in vivo. A vector generally contains at least an origin of replication for propagation in a cell. Control elements, including expression control elements as set forth herein, present within a vector, are included to facilitate transcription.

Vectors can include a selection marker. As is known in the art, "selection marker" refers to genes that allow the selection of cells containing the gene. "Positive selection" refers to selecting the cells that survive (contain the positive selection marker) upon exposure to the positive selection agent. For example, drug resistance is a common positive selection marker; cells containing the positive selection marker will survive in culture medium containing the selection drug, and those which do not contain the resistance gene will die. Suitable drug resistance genes are neo, which confers resistance to G418, or hygr, which confers resistance to hygromycin, or puro, which confers resistance to puromycin. Other positive selection marker genes include genes that allow the sorting or screening of cells. These genes include genes for fluorescent proteins, the lacZ gene, the alkaline phosphatase gene, and cell surface markers such CD8 (isolate positive cells by CD8 antibody panning), among others. "Negative selection" refers to a process whereby cells containing a negative selection marker are killed upon exposure to an appropriate negative selection agent which kills cells containing the negative selection marker. For example, cells which contain the herpes simplex virus-thymidine kinase (HSV-tk) gene are sensitive to the drug.

Vectors applicable in the invention are those based on viral vectors, such as simian virus 40 (SV40) or bovine papilloma virus (BPV), which has the ability to replicate as extra-chromosomal elements (Eukaryotic Viral Vectors, Cold Spring Harbor Laboratory, Gluzman ed., 1982; Sarver et al., *Mol. Cell. Biol.* 1:486 (1981)). Viral vectors include retroviral (lentivirus), adeno-associated virus (see, e.g., Okada (1996) *Gene Ther.* 3:957-964; Muzyczka (1994) *J. Clin. Invst.* 94:1351; U.S. Pat. Nos. 6,156,303; 6,143,548 5,952,221, describing AAV vectors; see also U.S. Pat. Nos. 6,004,799; 5,833,993), adenovirus (see, e.g., U.S. Pat. Nos. 6,140,087; 6,136,594; 6,133,028; 6,120,764), reovirus, herpesvirus, rotavirus genomes etc., modified for introducing and directing expression of a polynucleotide or transgene in cells. Retroviral vectors can include those based upon murine leukemia virus (see, e.g., U.S. Pat. No. 6,132,731), gibbon ape leukemia virus (see, e.g., U.S. Pat. No. 6,033,905), simian immunodeficiency virus, human immuno-deficiency virus (see, e.g., U.S. Pat. No. 5,985,641), and combinations thereof.

Vectors also include those that efficiently deliver genes to animal cells in vivo (e.g., stem cells) (see, e.g., U.S. Pat. Nos. 5,821,235 and 5,786,340; Croyle, M. A. et al., *Gene Ther.* 5:645 (1998); Croyle, M. A. et al., *Pharm. Res.* 15:1348 (1998); Croyle, M. A. et al., *Hum. Gene Ther.* 9:561 (1998); Foreman, P. K. et al, *Hum. Gene Ther.* 9:1313 (1998); Wirtz, S. et al., *Gut* 44:800 (1999)). Adenoviral and adeno-associated viral vectors suitable for in vivo delivery are described, for example, in U.S. Pat. Nos. 5,700,470, 5,731,172 and 5,604,090. Additional vectors suitable for in vivo delivery include herpes simplex virus vectors (see, e.g., U.S. Pat. No. 5,501,979), retroviral vectors (see, e.g., U.S. Pat. Nos. 5,624, 820, 5,693,508 and 5,674,703; and WO92/05266 and WO92/14829), bovine papilloma virus (BPV) vectors (see, e.g., U.S. Pat. No. 5,719,054), CMV-based vectors (see, e.g., U.S. Pat. No. 5,561,063) and parvovirus, rotavirus and Norwalk virus vectors. Lentiviral vectors are useful for infecting dividing as well as non-dividing cells (see, e.g., U.S. Pat. No. 6,013,516).

Vectors for insect cell expression commonly use recombinant variations of baculoviruses and other nucleopolyhedrovirus, e.g., *Bombyx mori* nucleopolyhedrovirus vectors (see, e.g., Choi (2000) Arch. Virol. 145:171-177). For example, Lepidopteran and Coleopteran cells are used to replicate baculoviruses to promote expression of foreign genes carried by baculoviruses, e.g., *Spodoptera frugiperda* cells are infected with recombinant *Autographa californica* nuclear polyhedrosis viruses (AcNPV) carrying a heterologous, e.g., a human, coding sequence (see, e.g., Lee (2000) J. Virol. 74:11873-11880; Wu (2000) J. Biotechnol. 80:75-83). See, e.g., U.S. Pat. No. 6,143,565, describing use of the polydnavirus of the parasitic wasp *Glyptapanteles indiensis* to stably integrate nucleic acid into the genome of Lepidopteran and Coleopteran insect cell lines. See also, U.S. Pat. Nos. 6,130,074; 5,858,353; 5,004,687.

Expression vectors capable of expressing proteins in plants are well known in the art, and include, e.g., vectors from Agrobacterium spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

Introduction of nucleic acid and polypeptide in vitro, ex vivo and in vivo can also be accomplished using other techniques. For example, a polynucleotide comprising an expression control element in operable linkage with a nucleic acid encoding Bcl-B protein can be incorporated into particles or a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A polynucleotide can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid drug delivery system. Colloidal dispersion systems include macromolecule complexes, nanocapsules, microspheres, beads, and lipid-based systems, including oil-in-water emulsions, micelles, mixed micelles, and liposomes. The use of liposomes for introducing various compositions, including polynucleotides, is known to those skilled in the art (see, e.g., U.S. Pat. Nos. 4,844,904, 5,000, 959, 4,863,740, and 4,975,282). A carrier comprising a natural polymer, or a derivative or a hydrolysate of a natural polymer, described in WO 94/20078 and U.S. Pat. No. 6,096, 291, is suitable for mucosal delivery of molecules, such as polypeptides and polynucleotides. Piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, vector (viral and non-viral, e.g., naked DNA) and non-vector means of delivery into mucosal cells or tissue, in vitro, in vivo and ex vivo can be achieved and are contemplated.

As used herein, the term "transgene" means a polynucleotide that has been introduced into a cell or organism by artifice. For example, in a host cell having a transgene, the transgene has been introduced by genetic manipulation or "transformation" of the cell. A cell or progeny thereof into which the transgene has been introduced is referred to as a "transformed cell" or "transformant." Typically, the transgene is included in progeny of the transformant or becomes a part of the organism (tissue or organs) that develops from the cell. Transgenes may be inserted into the chromosomal DNA or maintained as a self-replicating plasmid, YAC, minichromosome, or the like. Transgenes include any gene that is transcribed into an antisense or encodes a polypeptide.

A "host cell" includes a cell that expresses a composition of the invention. Host cells include cultured cells (cells that have been adapted for growth in vitro) and primary cells isolated from an organism manipulated to contain a composition of the invention. Host cells also can be present in an animal (subject), either by ex vivo manipulation of cells, transgenic introduction of compositions (non-human animals), or by in vivo introduction of a composition of the invention.

The term "subject" refers to an animal. Typically, the animal is a mammal, however, any animal in which Bcl-B is present or may modulate apoptosis is encompassed by the term. Specific examples are primates (humans), dogs, cats, horses, cows, pigs, and sheep. Subjects include those having a physiological disorder associated with apoptosis or at risk of developing a disorder associated with apoptosis, although they may not exhibit symptoms of the disorder. Subjects therefore may have a disorder associated with apoptosis or may not. At risk subjects can be identified by screening for genes associated with the disorders; over or under expression of a gene (e.g., caspase, fas, etc.) indicates a subject at risk for a disorder.

The term "antibody" or "Ab" includes both intact antibodies having at least two heavy (H) chains and two light (L) chains inter-connected by disulfide bonds and antigen binding fragments thereof, or equivalents thereof, either isolated from natural sources, recombinantly generated or partially or entirely synthetic. Examples of antigen binding fragments include, e.g., Fab fragments, F(ab')2 fragments, Fd fragments, dAb fragments, isolated complementarity determining regions (CDR), single chain antibodies, chimeric antibodies, partially humanized antibodies, human antibodies made in non-human animals (e.g., transgenic mice) or any form of antigen binding fragment.

As used herein, the term "bind" or "binding" means that the components referred to specifically interact with each other at a molecular level. Direct binding means physical contact between the components. Indirect binding means binding to one or more components that bind. Thus, the two components need not physically contact each other in order to bind as they may be a part of an oligomeric complex in which an intermediary component binds between the two components. Indirect or direct binding may be relatively stable, such as that which occurs between an antibody and an antigen or be less stable, e.g. a dissociation constant ($K_D$) of less than about $10^{-6}$. Binding may also be transient, such as the binding that occurs between a transcription factor and DNA for transcription initiation, which does not occur in the absence of transcription. "Specific binding" is where the binding is selective between the components. Specific binding can be detected using methods known in the art, for example, by immunoprecipitation, affinity chromatography, gel shift assays, gene expression assays, etc. "Specific" and "non-specific" binding can be distinguished using appropriate controls.

The terms "array," "microarray," "DNA array" or "nucleic acid array" or "biochip" as used herein mean a plurality of target elements, each target element comprising a defined amount of one or more biological molecules (e.g., nucleic acid, protein, drugs, small organic compounds, natural compounds, libraries thereof, etc.), including the Bcl-B nucleic acids or proteins of the invention, immobilized on a substrate (e.g., solid or semi-solid, permeable or non-permeable surface) for binding with sample nucleic acids, proteins, antibodies, test agents, drugs, organic or natural compounds. The Bcl-B proteins, nucleic acids, antibodies of the invention and subsequences thereof can be incorporated into any form of microarray, such as those described, e.g., in U.S. Pat. Nos. 6,045,996; 6,022,963; 6,013,440; 5,959,098; 5,856,174; 5,770,456; 5,556,752; 5,143,854.

The term "plant" includes whole plants, plant parts (e.g., leaves, stems, flowers, roots, etc.), plant protoplasts, seeds and plant cells and progeny of same, including progeny obtained through cuttings or through regeneration of a plant or plant tissue from a plant cell. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. Plantlets are also included within the meaning of "plant." Suitable plants for use in the invention include any plants amenable to transformation techniques, including both monocotyledonous and dicotyledonous plants. Examples of monocotyledonous plants include, but are not limited to, asparagus, field and sweet corn, barley, wheat, rice, sorghum, onion, pearl millet, rye and oat, and ornamentals.

Examples of dicotyledonous plants include, but are not limited to, tomato, potato, arabidopsis, tobacco, cotton, rapeseed, field beans, soybeans, peppers, lettuce, peas, alfalfa, clover, cole crops or Brassica (e.g., cabbage, broccoli, cauliflower, brussel sprouts), radish, carrot, beets, eggplant, spinach, cucumber, squash, melons, cantaloupe, sunflowers and various ornamentals. The term "plant cell", as used herein, refers to protoplasts, gamete producing cells, and cells that are capable of regenerating into whole plants. Accordingly, a seed comprising multiple plant cells capable of regenerating into a whole plant is included in the definition of "plant cell". As used herein, "plant tissue" includes differentiated and undifferentiated tissues of a plant, including but not limited to roots, stems, shoots, leaves, pollen, seeds, tumor tissue and various forms of cells and culture such as single cells, protoplast, embryos, and callus tissue.

A "biotic insult," as used herein, refers to plant challenge caused by viable or biologic agents (biotic agents), such as insects, fungi, bacteria, viruses, nematodes, viroids, mycoplasmas, and the like.

An "abiotic insult," as used herein, refers to plant challenge by a non-viable or non-living agent (abiotic agent). Abiotic agents that can cause challenge include, for example, environmental factors such as low moisture (drought), high moisture (flooding), nutrient deficiency, radiation levels, air pollution (ozone, acid rain, sulfur dioxide, etc.), temperature (hot and cold extremes), and soil toxicity, as well as herbicide damage, pesticide damage, or other agricultural practices (e.g., over-fertilization, improper use of chemical sprays, etc.).

The term "pathogen" refers to any biological organism or chemical agent produced by a biological organism that causes a disease or disease state in an animal or plant, including, but not limited to viruses, fungi, bacterium, nematodes, and other related microorganisms.

"Functional subsequences," which are portions of the compositions of the invention that retain at least one activity or function, all or in part, of the native full-length composition are included. "Functional subsequences" therefore include portions of Bcl-B protein (e.g., fragments of SEQ ID NO:2) which modulate apoptosis, bind to Bax, Bcl-2 and Bcl-$X_L$, associate with mitochondria or form a membrane channel alone or in combination with other Bc-2 protein family members. Functional subsequences also include subsequences that are immunogenic.

Bcl-B protein include peptides comprising amino acid sequences sufficiently homologous to or derived from the amino acid sequence of SEQ ID NO:2, which include less amino acids than the full length Bcl-B, and exhibit all or part of at least one activity of a Bcl-B protein (e.g., apoptosis modulating activity). Typically, an active portion comprises a domain or motif with at least one activity of the Bcl-B protein, for example, a domain or motif capable of modulating apoptosis; a domain or motif capable of interacting with a binding molecule, such as itself, Bax, Bcl-2 or Bcl-$X_L$; a domain or motif capable of associating with mitochondria, such as Bcl-B transmembrane domain; a domain or motif capable of modulating an intracellular molecule (e.g., Bax) that participates in an apoptotic signaling pathway; a domain or motif capable of forming a membrane channel alone, or in combination with other Bc-2 protein family members; a domain or motif capable of modulating a caspase; a domain or motif capable of modulating DNA fragmentation, chromatin condensation or other processes associated with apoptosis; or a domain or motif capable of modulating cell proliferation, survival, growth or differentiation.

A biologically active portion of a Bcl-B protein can be a polypeptide which is, for example, 10, 25, 50, 100 or more amino acids in length. Biologically active portions can be used directly as agents that modulate apoptosis or other activities of full length Bcl-B. Bcl-B protein can also be used as targets for developing agents which modulate a Bcl-B mediated activity, e.g., an activity described herein, and are potential therapeutics for treating disorders associated with undesirable or insufficient/deficient apoptosis.

The terms percent "sequence identity" or "sequence homology," in the context of two or more nucleic acids or polypeptide sequences, refers to sequences or subsequences thereof that have a specified percentage of nucleotides (or amino acid residues) that are the same, when compared and aligned for maximum correspondence over a comparison window. Percent identity can be measured by manual alignment and visual inspection or using a sequence comparison algorithm, as described herein. This definition also refers to the complement (antisense strand) of a sequence.

For example, in various embodiments, polypeptides of the invention include those having an amino acid sequence at least about 70%, at least about 80%, at least about 90%, at least about 95% and at least about 99% identical to an exemplary sequence set forth in SEQ ID NO:2. Polypeptide subsequences are also included. In additional embodiments, a subsequence is at least about 15, 20, 25, 30, 40, 50, 75, 125, 150 or 200, or greater amino acids (e.g., 300, 350, 400, 450, 500, 550, etc.) in length. Thus, a polypeptide sequence having the requisite sequence identity to SEQ ID NO:2, or a subsequence thereof, also is a polypeptide of the invention. In various additional embodiments, the polypeptides, including subsequences have one or more activities of a sequence set forth in SEQ ID NO:2. Thus, in various aspects a polypeptide has apoptosis modulating activity, oligomerization (heteromerizes or forms homodimers, trimers, etc.) activity, binds to Bcl-2, B Nucleic acids of the invention include those having at least about 70%, at least about 80%, at least about 90%, at least about 95%, and at least about 99% identity to the exemplary sequence set forth in SEQ ID NO:1, wherein the sequence is distinct from Accession no. AA098865. Thus, if a nucleic acid sequence has the requisite sequence identity to SEQ ID NO:1, or a subsequence thereof, it also is a polynucleotide sequence of the invention. In various aspects, the sequence is less than about 50 Kb, 25 Kb, 10 Kb, 5 Kb or 2.5 Kb. In additional aspects, the sequence is between about 2.5-1.0 Kb, 1.0-0.5 Kb, 0.25-0.1 Kb and 100-15 base pairs. In yet other aspects, the sequence is selected from SEQ ID NO:1; SEQ ID NO:1 where one or more T's are U's; nucleic acids complementary to these sequences and subsequences of the aforementioned sequences at least 15 base pairs long.

In one aspect, the percent identity exists over a region of the sequence that is at least about 25 nucleotides or amino acid residues in length, or, over a region that is at least about 50 to 100 nucleotides or amino acids in length. Parameters (including, e.g., window sizes, gap penalties and the like) to be used in calculating "percent sequence identities" between two nucleic acids or polypeptides to identify and determine whether one is within the scope of the invention are described in detail, below.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1-6.3.6. Hybridization stringency typically depends on the stringency of the wash. A particular example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Highly stringent conditions include one or more washes in 0.2×SSC, 0.1% SDS at 65° C. following the hybridization.

Sequences included in the invention are those that hybridize to exemplary Bcl-B sequence set forth in Example 1 (SEQ ID NO:1). Such sequences may be the entire length of the sequence, or may be fragments. For example, in various embodiments, the sequence that hybridizes has a length of about 12-30, 30-50, 50-100, 100-250, 250-500, 500-1000, 1000-2500, 2500-5000 or 5000-10000 base pairs. Such sequences are also distinct from Accession no. AA098865.

Such sequences are useful as probes, for example, to detect the presence or amount of Bcl-B in a sample; to detect a disorder associated with apoptosis where under or over expression of Bcl-B is indicative of the disorder (or indicative of a predisposition to the disorder); for identifying other Bcl-B family genes in mammalian (e.g., human) or other organisms, e.g., bacteria, plant, insect, yeast, etc. Such sequences are also useful as antisense. For example, sequences that hybridize to double strand Bcl-B (e.g., genomic Bcl-B) form a triplex nucleic acid molecule thereby inhibiting expression of the target Bcl-B. Double stranded RNA sequences (known as "RNAi") for inhibiting gene expression in organisms are also applicable and are known in the art (Kennerdell et al, *Cell* 95:1017-1026 (1998); Fire et al., *Nature*, 391:806-811 (1998)). Such antisense sequences can interfere with Bcl-B protein activity or expression and in turn increase apoptosis, or decrease cell survival or proliferation.

The invention further provides chimeric polypeptides comprising an amino acid sequence of the invention, for example, a sequence having at least about 65% identity to SEQ ID NO:2, and a second polypeptide sequence. Thus, peptides and polypeptides of the invention are synthesized and expressed as chimeric or "fusion" proteins with one or more additional domains linked thereto for, e.g., to more readily isolate or identify a recombinantly synthesized peptide, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and GCA-associated peptide or polypeptide can be useful to facilitate purification. For example, an expression vector can include an epitope-encoding nucleic acid sequence linked to six histidine residues followed by a thioredoxin and an enterokinase cleavage site (see, e.g., Williams (1995) Biochemistry 34:1787-1797; Dobeli (1998) Protein Expr. Purif. 12:404-14). The histidine residues facilitate detection and purification while the enterokinase cleavage site provides a means for purifying the epitope from the remainder of the fusion protein.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer). The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234. Modified peptides of the invention can be further produced by chemical modification methods, see, e.g., Belousov (1997) Nucleic Acids Res. 25:3440-3444; Frenkel (1995) Free Radic. Biol. Med. 19:373-380; Blommers (1994) Biochemistry 33:7886-7896.

The invention further provides isolated or recombinant nucleic acids comprising a nucleic acid sequence having at least about 80% sequence identity to SEQ ID NO:1, further including expression cassettes (e.g., vectors), cells and transgenic animals comprising the nucleic acids of the invention. As the genes and vectors of the invention can be made and expressed in vitro or in vivo, the invention provides for a variety of means of making and expressing these genes and vectors. One of skill will recognize that desired phenotypes associated with altered gene activity can be obtained by modulating the expression or activity of the genes and nucleic acids (e.g., promoters) within the expression cassettes (e.g., vectors) of the invention. Any of the known methods described for increasing or decreasing expression or activity can be used for this invention. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to insect and bacterial cells, e.g., mammalian, yeast or plant cell expression systems.

Alternatively, these nucleic acids can be synthesized in vitro by well-known chemical synthesis techniques, as described in, e.g., Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Expression control elements, which, are operably linked to the coding sequence for the exemplary polypeptide of the invention, SEQ ID NO:2 (or antisense), including promoters, comprising the genomic sequences 5' (upstream) of a transcriptional start site (see SEQ ID NO:1), enhancers and intronic sequences are readily available in the art or can be obtained using routine molecular biological techniques (e.g., cell expression assays). Methods for further characterization of promoter sequences include those general methods described by, e.g., Pang (1997) Biotechniques 22:1046-1048; Gobinda (1993) PCR Meth. Applic. 2:318; Triglia (1988) Nucleic Acids Res. 16:8186; Lagerstrom (1991) PCR Methods Applic. 1:111; Parker (1991) Nucleic Acids Res. 19:3055. As is apparent to one of ordinary skill in the art, these techniques can also be applied to identify, characterize and isolate any expression control sequences corresponding to or associated with the nucleic acid and polypeptide sequences of the invention.

The invention provides oligonucleotide primers that can amplify all or any specific region within a nucleic acid sequence of the invention, particularly, the exemplary SEQ ID NO:1. The nucleic acids of the invention can also be mutated, detected, generated or measured quantitatively using amplification techniques. Using the nucleic acid sequences of the invention (e.g., as in the exemplary SEQ ID NO:1), the skilled artisan can select and design suitable oligonucleotide amplification primers. Amplification methods are also known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y.); ligase chain reaction (LCR) (see, e.g., Barringer (1990) Gene 89:117); transcription amplification (see, e.g., Kwoh (1989) Proc. Natl. Acad. Sci. USA, 86:1173); and, self-sustained sequence replication (see, e.g., Guatelli (1990) Proc. Natl. Acad. Sci. USA, 87:1874); Q Beta replicase amplification (see, e.g., Smith (1997) J. Clin. Microbiol. 35:1477-1491; Burg (1996) Mol. Cell. Probes 10:257-271) and other RNA polymerase mediated techniques (e.g., NASBA, Cangene, Mississauga, Ontario).

The invention provides transformed cells comprising a nucleic acid of the invention. The cells can be mammalian (such as human), insect (such as *Spodoptera frugiperda*, *Spodoptera exigua*, *Spodoptera littoralis*, *Spodoptera litura*, *Pseudaletia separata*, *Trichoplusia ni*, *Plutella xylostella*, *Bombyx mori*, *Lymantria dispar*, *Heliothis virescens*, *Autographica californica* and other insect, particularly lepidopteran and coleopteran, cell lines), plant, bacteria, yeast, etc. Techniques for transforming and culturing cells are well described in the scientific and patent literature; see, e.g., Weiss (1995) Methods Mol. Biol. 39:79-95, describing insect cell culture in serum-free media; Tom (1995) Methods Mol. Biol. 39:203-224; Kulakosky (1998) Glycobiology 8:741-745; Altmann (1999) Glycoconj. J. 16:109-123; Yanase (1998) Acta Virol. 42:293-298; U.S. Pat. Nos. 6,153,409; 6,143,565; 6,103,526.

The invention also provides transgenic animals, including non-human mammals and insects. Insects stably expressing the nucleic acids of the invention can be to study apoptosis, screening for modulators of apoptosis and caspases, manipulation of insect life cycles, such as *Bombyx mori* and its use in silk production. The nucleic acids of the invention can be expressed in a variety of insect larvae, e.g., *Bombyx mori* (see, e.g., Maeda (1985) Nature 315: 592-594), *Trichoplusia ni*, the cabbage looper larvae (Medin (1990) Proc. Nat. Acad. Sci. USA 87: 2760-2764) and *Manduca sexta*, the tobacco hornworm (U.S. Pat. No. 5,471,858). See, e.g., Keshan (2000) J. Insect Physiol. 46:1061-1068; U.S. Pat. No. 5,118,616.

Non-human transgenic mammals include, e.g., primates (chimps, apes, macaques, orangutans), cows, goats, horses, sheep, pigs, rats, rabbits and mice, comprising the nucleic acids of the invention. These animals can be used, e.g., as in vivo models to study apoptosis and potential therapies for apoptosis. For example, animal models that mimic human apoptotic disorders (e.g., cell degeneration or proliferation, such as that of neural or muscular tissue, or cancer), can be used to study whether Bcl-B compositions of the invention ameliorate (relieve or improve one or more symptoms, e.g., inhibit additional cell death or degeneration) of the disorder. Such models can be used to screen for agents that modulate Bcl-B activity in vivo. Transgenic non-human animals can be designed and generated using any method known in the art; see, e.g., U.S. Pat. Nos. 6,156,952; 6,118,044; 6,111,166; 6,107,541; 5,959,171; 5,922,854; 5,892,070; 5,880,327; 5,891,698; 5,639,940; 5,573,933, describing making and using transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats.

The invention also provides transgenic plants, including seeds, expressing the Bcl-B nucleic acids and polypeptides of the invention. Nucleic acids may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Microprojectile bombardment to deliver DNA into plant cells is an alternative means of transformation for the numerous species considered recalcitrant to *Agrobacterium*- or protoplast-mediated transformation methods. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, U.S. Pat. Nos. 5,608,148 and 5,681,730, describing particle-mediated transformation of gymnosperms.

Alternatively, transformed plant cells can be generated by fusion of the recipient cells with bacterial protoplasts containing DNA, use of DEAE dextran, polyethylene glycol precipitation, as described, e.g., in Paszkowski (1984) EMBO J. 3:2717-2722. DNA construct can be introduced directly into the genomic DNA of the plant cell using electroporation, as described, e.g., in Fromm (1985) Proc. Natl. Acad. Sci. USA 82:5824, or by microinjection of plant cell protoplasts, as described, e.g., Schnorf (1991) Transgenic Res. 1:23-30.

DNA can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) Science 233:496-498; Fraley (1983) Proc. Natl. Acad. Sci. USA 80:4803 (1983); *Gene Transfer to Plants*, Potrykus, ed. (Springer-Verlag, Berlin 1995).

The nucleic acid sequences of the invention include genes and gene products identified and characterized by analysis using the exemplary protein and nucleic acid sequences of the invention, including SEQ ID NO:2 and SEQ ID NO:1. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used unless alternative parameters are designated herein. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned.

Methods of sequence alignment for comparison are well-known in the art. Optimal alignment of sequences can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (CLUSTAL, GAP, BESTFIT, FASTA, and TFASTA in the Wisconsin Genetics Software Package, Genetics Computer Group, 575 Science Dr., Madison, Wis.), or by manual alignment and visual inspection.

In one aspect of the invention, a CLUSTAL algorithm, such as the CLUSTAL W program, is used to determine if a nucleic acid or polypeptide sequence is within the scope of the invention; see, e.g., Thompson (1994) *Nuc. Acids Res.* 22:4673-4680; Higgins (1996) *Methods Enzymol* 266:383-402. Variations of this aspect can also be used, such as CLUSTAL X, see Jeanmougin (1998) *Trends Biochem Sci* 23:403-405; Thompson (1997) *Nucleic Acids Res* 25:4876-4882. CLUSTAL W program, described by Thompson (1994) supra, in the methods of the invention used with the following parameters: K tuple (word) size: 1, window size: 5, scoring method: percentage, number of top diagonals: 5, gap penalty: 3.

Another algorithm is PILEUP, which can be used to determine whether a polypeptide or nucleic acid has sufficient sequence identity to SEQ ID NO:1 or SEQ ID NO:2 to be with the scope of the invention. This program creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, CABIOS 5:151-153 (1989). The following parameters are used with PILEUP in the methods of the invention: default gap weight (3.00), default gap length weight (0.10), and weighted end gaps.

Another example of an algorithm suitable for determining percent sequence identity (i.e., substantial similarity or identity) in the invention is the BLAST algorithm, which is described in Altschul (1990) *J. Mol. Biol.* 215:403-410. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

The invention provides antibodies that specifically bind to the Bcl-B polypeptides of the invention, e.g., the exemplary SEQ ID NO:2. These antibodies can be used, e.g., to isolate the polypeptides of the invention, to identify the presence of Bcl-B polypeptides that modulate apoptosis, and the like. To generate antibodies, Bcl-B polypeptides or peptides (antigenic fragments of SEQ ID NO:2) can be conjugated to another molecule or can be administered with an adjuvant. The coding sequence can be part of an expression cassette or vector capable of expressing the immunogen in vivo (see, e.g., Katsumi (1994) *Hum. Gene Ther.* 5:1335-9). Methods of producing polyclonal and monoclonal antibodies are known to those of skill in the art and described in the scientific and patent literature, see, e.g., Coligan, CURRENT PROTOCOLS IN IMMUNOLGY, Wiley/Greene, NY (1991); Stites (eds.) BASIC AND CLINICAL IMMUNOLOGY (7th ed.) Lange Medical Publications, Los Altos, Calif.; Goding, MONOCLONAL ANTIBODIES: PRINCIPLES AND PRACTICE (2d ed.) Academic Press, New York, N.Y. (1986); Harlow (1988) ANTIBODIES, A LABORTAROY MAnnual, Cold Spring Harbor Publications, New York.

Antibodies also can be generated in vitro, e.g., using recombinant antibody binding site expressing phage display libraries, in addition to the traditional in vivo methods using animals. See, e.g., Huse Science 246:1275 (1989); Ward Nature 341:544 (1989); Hoogenboom Trends Biotechnol. 15:62-70 (1997); Katz Annu. Rev. Biophys. Biomol. Struct. 26:27-45 (1997). Human antibodies can be generated in mice engineered to produce only human antibodies, as described by, e.g., U.S. Pat. Nos. 5,877,397; 5,874,299; 5,789,650; and 5,939,598. B-cells from these mice can be immortalized using standard techniques (e.g., by fusing with an immortalizing cell line such as a myeloma or by manipulating such B-cells by other techniques to perpetuate a cell line) to produce a monoclonal human antibody-producing cell. See, e.g., U.S. Pat. Nos. 5,916,771 and 5,985,615.

As discussed, the invention includes Bcl-B polypeptides having apoptosis modulating activity, including subsequences and sequence variants (e.g., a polypeptide having at least about 65% identity to SEQ ID NO:2), including mimetics etc., having apoptosis modulating activity. In addition, the invention provides methods for identifying an agent that modulates an activity of a polypeptide of the invention (e.g., a Bcl-B polypeptide having apoptosis modulating activity) that is capable inhibiting apoptosis in a cell.

Determining the amount or degree of apoptosis in a cell can be measured using routine in vitro or cell based techniques described herein or known in the art. For example, the amount or degree of activity can be determined by expressing a test Bcl-B polypeptide in a cell and measuring apoptosis in the cell (e.g., see Example 1 where percent apoptotic cells is determined by counting cells having nuclear fragmentation or chromatin condensation). Caspase protease activity in a cell generally reflects apoptosis and, therefore, increasing caspase activity or expression indicates increased cell apoptosis. Additional assays include measuring the amount or degree of DNA fragmentation in a cell; the amount or degree of cleavage of caspase substrates in a cell; or by measuring the amount or degree of any surrogate marker of apoptosis in the cell. In vitro and cell based assay can be performed alone or in association with other pro- or anti-apoptotic proteins. Methods for measuring apoptosis are described, for example, in Methods in Enzymology (2000) volume 322, edited by John C. Reed, Academic Press, e.g., chapters on pages 3, 15, 41, describing assays to measure apoptosis and surrogate markers of apoptosis and enzymes with activity related to levels of apoptosis, e.g., assays to determine DNA fragmentation, caspase assays, measuring annexin V (see, e.g., Zhang (1997) Biotechniques 23:525-531), and the like. See, e.g., van Engeland (1996) Cytometry 24:131-139; Gorczyca (1998) Methods Mol. Biol. 91:217-238. See also, e.g., U.S. Pat. Nos. 6,165,737; 6,165,732; 6,160,095; 6,143,522; 6,087,384; 6,077,684; 6,060,238; 6,054,436; 5,985,829; 5,976,786; 5,952,189. The invention incorporates all such methods and variations thereof.

The invention further provides kits comprising one or more compositions of the invention, including pharmaceutical compositions. In one embodiment, a kit contains one or more Bcl-B polypeptides or polynucleotide sequences encoding Bcl-B, and a label or packaging insert including instructions for expressing the polypeptide in cells (in vitro, ex vivo or in vivo) under conditions allowing increased expression of a target gene, in suitable packaging material. In another embodiment, a kit contains a Bcl-B antisense or ribozyme or DNAzyme or RNAi, and a label or packaging insert including instructions for expressing or introducing the antisense or ribozyme or DNAzyme or RNAi in cells (in vitro, ex vivo or in vivo) under conditions allowing decreased expression Bcl-B in the cell, in suitable packaging material.

As used herein, the term "packaging material" refers to a physical structure housing the components of the kit, such as Bcl-B polypeptides, polynucleotides and antibodies. The packaging material can maintain the components sterilely, and can be made of material commonly used for such purposes (e.g., paper, corrugated fiber, glass, plastic, foil, etc.). The label or packaging insert can include appropriate instructions, for example, practicing a method of the invention, e.g., treating a apoptotic disorder treatable by expressing a Bcl-B protein, antisense or ribozyme or DNAzyme or RNAi or antibody in vivo.

The invention also provides methods of treating disorders associated with apoptosis or with disorders in which apoptotic proteins participate. Disorders associated with apoptosis include disorders characterized by abnormal or undesirable, or increased or undesirable cell death, degeneration or insufficient/deficient or increased or undesirable cell growth, proliferation, survival or differentiation. Disorders in which apoptotic proteins participate are non-apoptotic disorders, but expression or activity of proteins associated with the disorder may exacerbate the disorder.

Examples of cellular proliferative or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of breast, colon, lung, and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon, liver and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Degenerative disorders include neuro-or muscular degeneration or atrophy. Such disorders afflict the brain and include, for example, Alzheimer's disease, Parkinson's disease, Creutzfeldt-Jacob's disease (CJD), Huntington disease (HD), Machado-Joseph disease (MJD), Spinocerebellar ataxias 1, 2 and 6 (SCA-1, -2 and -6), dentatorubropallidoluysian atrophy (DRPLA), Kennedy's disease, ischemia, stroke and head trauma.

Treatment generally results in reducing or preventing the severity or symptoms of the disorder in the subject, i.e., an improvement in the subject's condition or a "therapeutic effect." Therefore, treatment can reduce the severity or prevent one or more symptoms of the apoptotic disorder, inhibit progression or worsening of the disorder, and in some instances, reverse the disorder. Thus, in the case of a degenerative disorder, for example, treatment can prevent further degeneration resulting in a stabilization of the condition. Improvement in a cell proliferative disorder can mean inhibition of tumor growth, at least in part, such as to slow the progression of the tumor. This can also lead to an improvement in the subject because slowing the growth of a tumor generally results in prolonging life span of the patient or reducing the chances for metastasis, even though the subject may not be free of the tumor.

As used herein, the term "ameliorate" means an improvement in the subject's condition, a reduction in the severity of a disorder, or an inhibition of progression or worsening of the disorder.

The doses or "effective amount" for treating a subject are preferably sufficient to ameliorate one, several or all of the symptoms of the condition, to a measurable or detectable extent, although preventing or inhibiting a progression or worsening of the disorder or condition, or a symptom, is a satisfactory outcome. Thus, to ameliorate a disorder treatable by a method of the invention, that is, a disorder where modulating apoptosis results in an improvement, the effective amount will depend on the condition and the desired outcome and can be readily ascertained by the skilled artisan. Appropriate amounts will also depend upon the therapeutic effect desired, as well as the individual subject (e.g., the bioavailability within the subject, gender, age, etc.). The effective amount can be ascertained by measuring relevant physiological effects.

The methods of the invention for treating a subject are applicable for prophylaxis to prevent an apoptotic condition in a subject, such as a degenerative condition or an associated disorder. The methods of the invention for treating a subject also can be supplemented with other forms of therapy. Supplementary therapies include drug treatment (e.g., growth factor addition, chemotherapy, radiation treatment, surgical resection, etc.). The skilled artisan can readily ascertain therapies that may be used in combination with the treatment methods of the invention.

As the methods of the invention include methods of treating a subject, such as a human subject, the invention also provides "pharmaceutically acceptable" or "physiologically acceptable" formulations including one or more compositions of the invention alone, in combination with each other, or in combination with other drugs or agents suitable for treatment. Such formulations can be administered ex vivo or in vivo to a subject in order to practice the treatment methods of the invention, for example.

As used herein, the terms "pharmaceutically acceptable" and "physiologically acceptable" refer to carriers, diluents, excipients and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

A pharmaceutical formulation can be formulated to be compatible with its intended route of administration. Thus, pharmaceutical formulations include carriers, diluents, or excipients suitable for administration by routes including intraperitoneal, intradermal, subcutaneous, oral (e.g., ingestion or inhalation), intravenous, intracavity, intracranial, transdermal (topical), parenteral, e.g. transmucosal and rectal.

Solutions or suspensions used for parenteral, intradermal, or subcutaneous application can include the following: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical formulations suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, an the like. Isotonic agents, for example, sugars, polyalcohols such as mannitol, sorbitol, sodijm chloride can be included in the composition. Prolonged absorption of injetable formulations can be achieved by including an agent that delays absorption, for example, aluminum monostearate or gelatin.

For oral administration, a composition can be incorporated with excipients and used in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including implants and microencapsulated delivery systems. For example, a time delay material such as glyceryl monostearate or glyceryl stearate alone, or in combination with a wax, may be employed.

Additional formulations include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. Methods for preparation of such formulations will be apparent to those skilled in the art. The materials can also be obtained commercially from Alza Corporation and Nova Pharmaceuticals, Inc., for example.

The rate of release of a composition can be controlled by altering the concentration or composition of such macromolecules. For example, the composition can be entrapped in microcapsules prepared by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems including oil-in-water emulsions, micelles, mixed micelles, and liposomes. These can be prepared according to methods known to those skilled in the art, for example, as described in U.S. Pat. No. 4,522,811.

Additional pharmaceutical formulations appropriate for administration are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; and *Pharmaceutical Principles of Solid Dosage Forms*, Technonic Publishing Co., Inc., Lancaster, Pa., (1993)).

Injection needles, endoscopes, cannulas, intubation tubes, catheters and the like can be used to deliver the formulation to various parts of a subject. This allows effective delivery and targeting of vectors to particular areas within a subject.

All publications, patents and other references cited herein are incorporated by reference in their entirety. In case of conflict, the present specification, including definitions, will control. Unless defined otherwise herein, all technical and scientific terms used herein have the meaning commonly understood by a person skilled in the art to which this invention pertains.

As used herein, the singular forms "a", "and," and "the" include plural referents unless the context clearly indicates otherwise. Thus, for example, reference to "a transformed cell" includes a plurality of such cells and reference to "an isolated or recombinant polynucleotide" includes reference to one or more such sequences, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLE 1

This example describes the initial cloning of exemplary Bcl-B set forth in SEQ ID NO:1. This example also describes routine techniques for characterizing and analyzing Bcl-B activity.

Cloning of BCL-B cDNAs

A TBLASTN search of the human Expressed Sequence Tag (EST) database using the amino-acid sequence of the mouse Boo/Diva as a query resulted in the identification of homologous partial cDNAs. A human EST clone (Accession no. AA098865) was obtained (Research Genetics) and sequenced in its entirety, revealing an open reading frame (ORF) encompassing the last 151 residues of a protein with homology to Boo (Bcl-B). The corresponding genomic sequence for this cDNA was identified in the human genome database (clone CTD-2184D3), which was derived from human chromosome 15q21.

Because the EST clone lacked a candidate start codon, the corresponding 5'-end of Bcl-B cDNAs was cloned by a reverse-transcriptase polymerase chain reaction (RT-PCR) approach, using the forward primer NK01 18 (5'-CGGGC-CAAGAAAACCAGCGAAGG-3'; SEQ ID NO:7), which was designed to hybridize to a region upstream of the Bcl-B ORF as predicted from the genomic data, and the reverse primer NK0121 (5'-CACTCAAGGAAGAGCCATTTG-CAT-3'; SEQ ID NO:8), which is complementary to a region downstream of the predicted Bcl-B ORF corresponding to the 3'-untranslated region of the putative mRNA. PCR amplification using template human liver cDNA (Clontech) with the above primers yielded a single ~0.9 Kb product which was cloned into pCR2.1-TOPO (Invitrogen, following manufacturer's instructions) to generate TOPO-Bcl-B (pNK254) and sequenced. The cDNA containing the complete open reading frame (ORF) corresponding to a 204 amino-acid protein is shown in FIG. 1A.

Plasmid Construction

The ORF encoding Bcl-B was PCR-amplified from TOPO-Bcl-B (pNK254) using the forward primer NK0101 (5'-GGAATTCATGGTTGACCAGTTGCGGGAG-3'; SEQ ID NO:9) and reverse primer NK0103 (5'-CCGCTCGAGTCAT-AATAATCGTGTCCAGAG-3'; SEQ ID NO:10). The PCR products were digested with EcoRl and Xhol and cloned into the EcoRl and Xhol sites of pcDNA3-Myc (Stratagene), and the EcoRl and Sa/l sites of pcl-Neo-Flag (InVitrogen) and pEGFP-C2 (Clontech). A plasmid encoding Bcl-B lacking its C-terminal transmembrane domain (Bcl-BΔTM) was constructed by PCR-based mutagenesis using primers NK0101 and NK0131 (5'-CCGCTCGAGTCATGTTTTCTC-CAAAAAGCCAGTG-3'; SEQ ID NO:11). The resulting PCR product was digested with EcoRl and Xhol and cloned into pcDNA3-Myc.

RT-PCR an Analysis

Expression of BCL-B mRNA in various tissues was examined by RT-PCR, using oligo-dT primed first-strand cDNA derived from multiple adult human tissues (Clontech) as templates. cDNAs were amplified following manufacturer's instructions using the forward primer NK0120 (5'-GTGGT-GACGCTCGTGACCTTCG-3'; SEQ ID NO:12) and NK0121 as the reverse primer. G3PDH primers were used as a positive control (Kitada et al., Antisense Res. Dev. 4, 71-79 (1994)).

Cell Culture, Transfection, and Apoptosis Assays

HEK293, Cos7, HT1080 and PPC1 cells were maintained in Dulbecco's modified Eagle's medium (Irvine Scientific) supplemented with 10% fetal bovine serum, 1 mM L-glutamine, and antibiotics. For apoptosis assays, cells ($5 \times 10^5$) in 6-well dishes were co-transfected using Superfect (Qiagen) with 0.5 µg pcDNA3-Bax plus 0.5 µg of green fluorescence protein (GFP) marker plasmid pEGFP (CLONTECH) or 0.5 µg pEGFP-Bak, and 1 µg of pcDNA3, pcDNA3-Myc-Bcl-B, pcDNA3-Myc-Bcl-BΔTM, or pcDNA3-Flag-Bcl-XL. The total amount of DNA was 3 µg per transfection using pcDNA3. At 24 hrs post-transfection, both adherent and floating cells were collected, fixed and stained with 0.1 ug/ml 4',6-diamidino-2-phenylindole (DAPI). The percent of apoptotic cells were determined by counting the GFP-positive cells having nuclear fragmentation and/or chromatin condensation (Mean±S.D.; n=3).

Co-immunonreciaitation and Immunoblotting Assays 293T cells ($5 \times 10^6$) cultured with 50 uM benzoyl-Val-Ala-Asp-fluoromethylketone (ZVAD-fmk, Bachem) were co-transfected with 1.5 ug of pcDNA3-Myc-Bcl-B, pcl-Neo-Flag-Bcl-B, pcDNA3-hCBP (Human Calcyclin Binding Protein) (used as a control), or pcDNA3-Flag-BCl-$X_L$, together with 1.5 ug of pEGFP, pEGFP-Bcl-B, pcDNA3-HA-BAG1, pcDNA3-HA-Bax, pcDNA3-Flag-Bcl-$X_L$, pRC-CMV-Bcl-2 or pEGFP-Bak. At 24 hrs post-transfection, cells were collected and resuspended in lysis buffer (142.4 mM KCI, 5 mM $MgCl_2$, 10 MM HEPES (pH 7.4), 0.5 mM EGTA, 0.2% NP-40) containing 12.5 mM p-glycerophosphate, 2 mM NaF, 1 mM $Na_3VO_4$, 1 mM DTT, 1 mM PMSF and a protease inhibitor mixture (Boehringer Mannheim). Soluble lysates were incubated with 10 ul anti-Myc (Santa Cruz) or anti-Flag (Sigma) antibody conjugated Sepharose beads overnight at 4° C. Beads were washed four times in 1.5 ml lysis buffer, and boiled in Laemmli gel-loading solution before performing SDS-PAGE/immunoblotting. The following polyclonal or monoclonal antibodies were used: polyclonal rabbit anti-GFP (Roche), monoclonal rat anti-HA (Roche), monoclonal mouse anti-Flag (Sigma), monoclonal mouse anti-Myc (Santa Cruz), rabbit anti-huBcl-2, or rabbit anti-huBcl-XL (Krajewski, et al., Am. J. Pathol. 145, 515-525 (1994); Krajewski et al., Cancer Res. 54, 5501-5507 (1994)).

Immunofluorescence and Subcellular Fractionation

For immunofluorescence analysis, Cos7 cells were transfected with pEGFP-Bcl-B. At 24 hrs post-transfection, 50 uM Mitotracker Red CMXRos (Molecular Probes) was added to the cell cultures for 30 mins. The cells were washed with PBS and fixed with 4% formaldehyde before imaging by confocal microscopy using a Bio-Rad MRC 1024 instrument.

For subcellular fractionation experiments, 293T cells ($2\times10^6$) were transfected with 10 ug pcDNA3-Myc-Bcl-B, pcDNA3-Myc-Bcl-BΔTM, or pRC-CMV-Bcl-2. At 24 hrs post-transfection, cells were collected and lysed by homogenization in hypotonic buffer (5 mM Tris-CI, pH 7.4, 5 mM KCI, 1.5 mM $MgCl_2$) containing 1 mM PMSF and a mixture of other protease inhibitors (Boehringer Mannheim). The nuclear fraction was discarded by centrifugation at 500×g for 5 mins. The heavy membrane (HM) fraction was obtained by centrifugation of the post-nuclear lysates at 10,000×g for 20 mins. The resulting supernatant was either used directly or further centrifuged at 150,000×g for 90 mins to separate the light membrane fraction (LM) (pellet) from the cytosolic (C) (supernatant) fraction. Fractions were normalized to cell equivalents and analyzed by immunoblotting using antibodies specific for Myc-epitope tag (Santa Cruz) and Bcl-2, with Enhanced chemiluminescence (ECL) detection (Amersham Pharmacia Biotech).

EXAMPLE 2

This example describes structural characteristics of Bcl-B sequences. This example also describes expression patterns of Bcl-B in adult human tissue.

Exemplary Bcl-B nucleic acid sequence (SEQ ID NO:1) is as follows:

```
cgggccaaga aaaccagcga aggcccggcc ccccagcaga ggccggacca tggttgacca gttgcgggag cgcaccacca tggccgaccc gctgcgggag cgcaccgagc tgttgctggc cgactacctg gggtactgcg cccgggaacc cggcaccccc gagccggcgc catccacgcc cgaggccgcc gtgctgcgct ccgcggccgc caggttacgg cagattcacc ggtccttttt ctccgcctac ctcggctacc ccgggaaccg cttcgagctg
```

-continued

```
gtggcgctga tggcggattc cgtgctctcc gacagccccg gccccacctg gggcagagtg gtgacgctcg tgaccttcgc agggacgctg ctggagagag ggccgctggt gaccgcccgg tggaagaagt ggggcttcca gccgcggcta aaggagcagg agggcgacgt cgcccgggac tgccagcgcc tggtggcctt gctgagctcg cggctcatgg ggcagcaccg cgcctggctg caggctcagg gcggctggga tggcttttgt cacttcttca ggaccccctt tccactggct ttttggagaa aacagctggt ccaggctttt ctgtcatgct tgttaacaac agccttcatt tatctctgga cacgattatt atgagtttta aaactttaa cccgcttcta cctgcccaac tgtgaccaac taaatgacag atgtgtgaga acaagaactg agggaaagca ccttccccca ccccagacgt ttttatctga atgcatacaa ggagtcctga ggtggtgatt tggccagtgt tttaacttgt gacaagtact caggtgtgag gacaagaatg caaatggctc ttccttgagt gaaagaa
```

The predicted ORF was initiated by a AUG start codon within a favorable Kozak context. The protein contains regions resembling the BH1, BH2, BH3, and BH4 domains typical of anti-apoptotic members of the Bcl-2 family, as well as a putative carboxyl-terminal TM domain (FIG. 1B). Comparisons of this predicted sequence with all known Bcl-2 family members by BLAST search indicated that it is most similar to the murine Bcl-2-family protein Boo (also known as Diva; Song et al., EMBO J 18, 167-178 (1999); Inohara et al., J. Biol. Chem. 273, 32479-32486(1998)). Exemplary Bcl-B shares 47% amino-acid sequence identity with Boo.

The BCL-B gene is located on chromosome 15 (map 15q21), as determined by in silico screening of the human genome database at NCBI. Comparison of the BCL-B cDNA sequence with genomic data indicates a two exon structure, in which the region encoding residues Trp163 and Asp164 (within the BH2 domain) of the protein are interrupted by an ~2.3 kb intron.

Adult human tissues were analyzed for Bcl-B expression. In brief, first-strand cDNAs were made from RNA samples from adult human tissues and PCR-amplified using BCL-B-specific primers. The reverse primer was downstream of the intron to avoid amplification of contaminating genomic DNA. PCR products were size-fractionated by electrophoresis in 1% agarose gels, stained with ethidium bromide, and photographed under UV-illumination. Primers specific for glyceraldehyde-3-phosphate dehydrogenase (G3PDH) were also used for PCR as a positive control. The results indicate that BCL-B mRNA is widely expressed in adult human tissues (FIG. 1C). Greatest levels of expression were detected in liver, pancreas and spleen.

EXAMPLE 3

This example describes studies demonstrating that Bcl-B binds with itself as well as other Bcl-2 family proteins. This example also describes studies demonstrating that Bcl-B binding is selective for other proteins associated with the apoptotic signaling pathway.

In brief, 293T cells were transiently transfected with various combinations of plasmids encoding Myc-Bcl-B, Myc-hCBP, GFP, GFP-Bcl-B, GFP-Bak, Bcl-2, Flag-Bcl-$X_L$, HA-Bax, HA-BAG1 and Flag-Bcl-B. Cell lysates were prepared and immunoprecipitated as described above using either anti-Myc or anti-Flag monoclonal antibodies.

Figure 2:
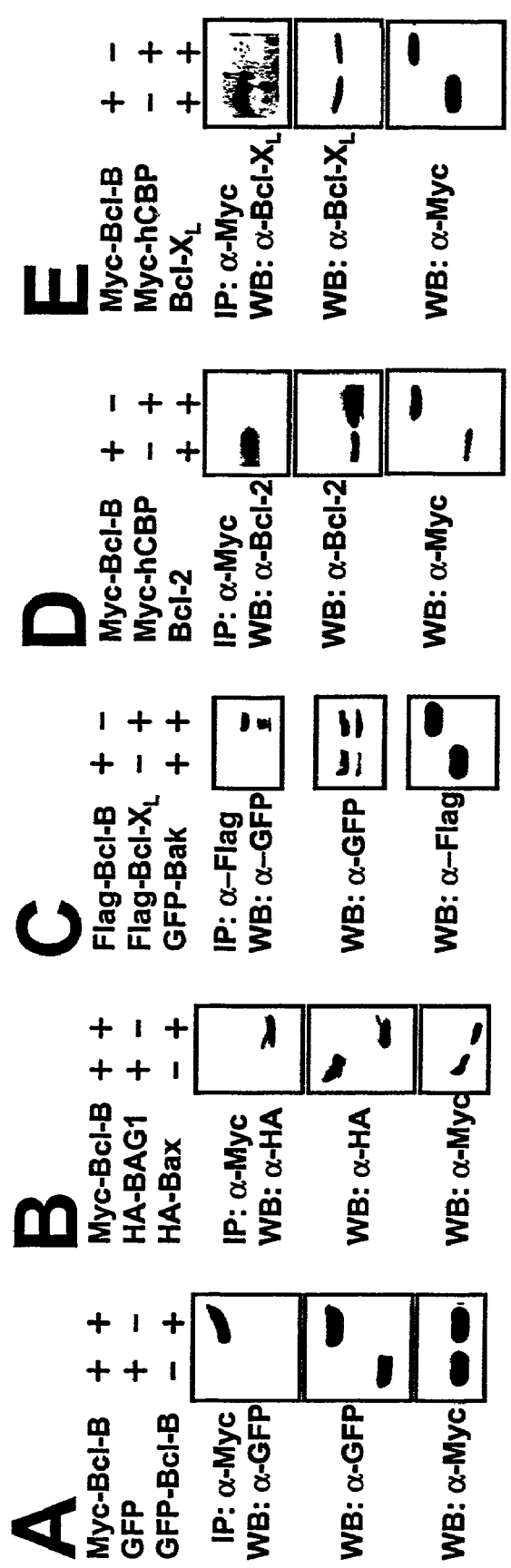
FIGS. 2A-2E show that Bcl-B interacts with itself and several Bcl-2 family proteins. Expressed chimeras Myc-Bcl-B, Myc-hCBP, GFP, GFP-Bcl-B, GFP-Bak, Bcl-2, Flag-Bcl-XL, HA-Bax, HA-BAG1 and Flag-Bcl-B were immunoprecipitated (IP) with anti-Myc or anti-Flag monoclonal antibodies and western blotted (WB) with antibodies specific for GFP, HA, Flag, Myc, or Bcl-XL.

Immunoprecipitated proteins were fractionated by SDS-PAGE and subjected to immunoblot analysis using rabbit polyclonal antibodies specific for GFP, Bcl-XL, or Bcl-2 or rat monoclonal antibody specific for HA (FIG. 2, top panel). To confirm expression of all proteins, equivalent volumes of lysates were also loaded directly in gels and analyzed by SIDS-PAGE/immunoblotting (FIG. 2, middle and bottom panels) using antibodies specific for GFP, HA, Flag, Myc, Bcl-XL, or Bcl-2. For efficiency of presentation, only the portion of the gels containing the relevant bands is shown. Additional controls, including immunoprecipitations using negative-control antibodies were also performed.

These results indicate that Bcl-B is capable of binding with itself, Bax, Bcl-2, and Bcl-XL, but not with Bak. These findings are consistent with Bcl-B suppressing Bax mediated cellular apoptosis, described in detail below.

EXAMPLE 4

This example describes data showing that Bcl-B inhibits apoptosis induced by Bax. This example also describes data showing that Bcl-B binding to Bax, at least in part, contributes to inhibiting apoptosis induced by Bax, and that Bcl-B does not detectably inhibit apoptosis induced by Bak.

The anti-apoptotic activity of Bcl-B was studied by transient transfection of a variety of cell lines, including HEK293T, Cos7 (monkey kidney cells), HT1080 and PPC1. In brief, HEK293T (FIG. 3A) and Cos-7 (FIG. 3B) cells at ~50% confluence in 6-well dishes were co-transfected with plasmids encoding GFP (0.5 ug) (used as a marker for transfection with Bax) and 0.5 ug of pcDNA3 (control), pcDNA3-Bax or pEGFP-Bak in combination with 1 ug (two-fold excess) of pcDNA3, pcDNA-3-Myc-Bcl-B or pcDN3-Flag-Bcl-$X_L$. After 24 hrs posttransfection, cells were collected and stained with DAPI. The percentage of GFP-positive cells with apoptotic morphology (fragmented nuclei or condensed chromatin) was determined (mean+SD; n=3). Immunoblotting of control cultures supplemented with 50 uM zVAD-fmk to prevent apoptosis confirmed production of all proteins (as described in Example 3). Similar results were also obtained with HT1080 and PPC1 cells.

Bcl-B over-expression did not induce apoptosis in any of the cell lines. Bcl-B also did not suppress apoptosis caused by over-expressing Bcl-2 or Bcl-$X_L$. These data therefore indicate that Bcl-B is not a proapoptotic protein (induces or stimulates apoptosis) in these particular cell lines.

Figure 3:
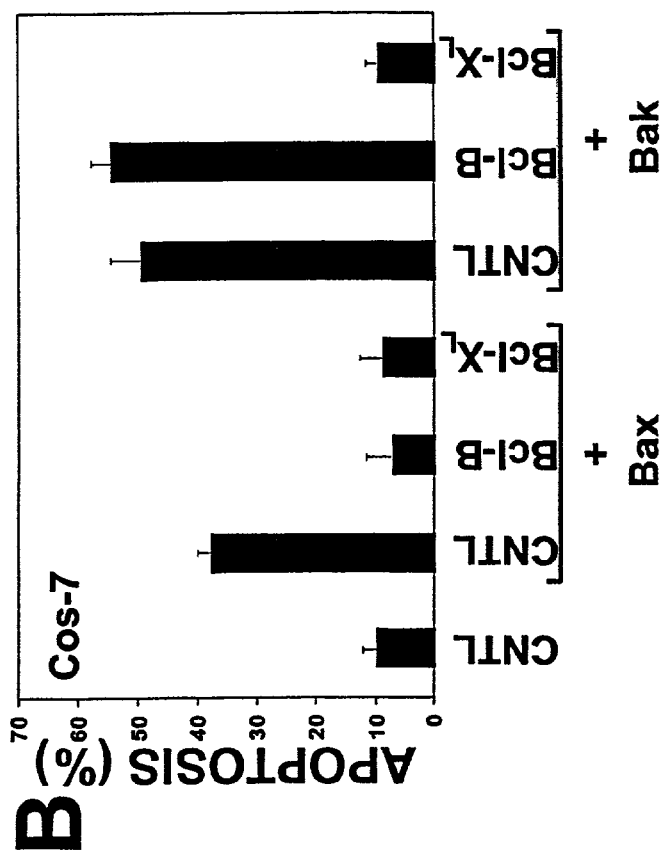
FIG. 3 shows that Bcl-B inhibits Bax- but not Bak-induced apoptosis in (A) 293T and (B) Cos-7 cells. The percentage of GFP-positive cells with apoptotic morphology (fragmented nuclei or condensed chromatin) was determined (mean±SD; n=3).
Figure 3:
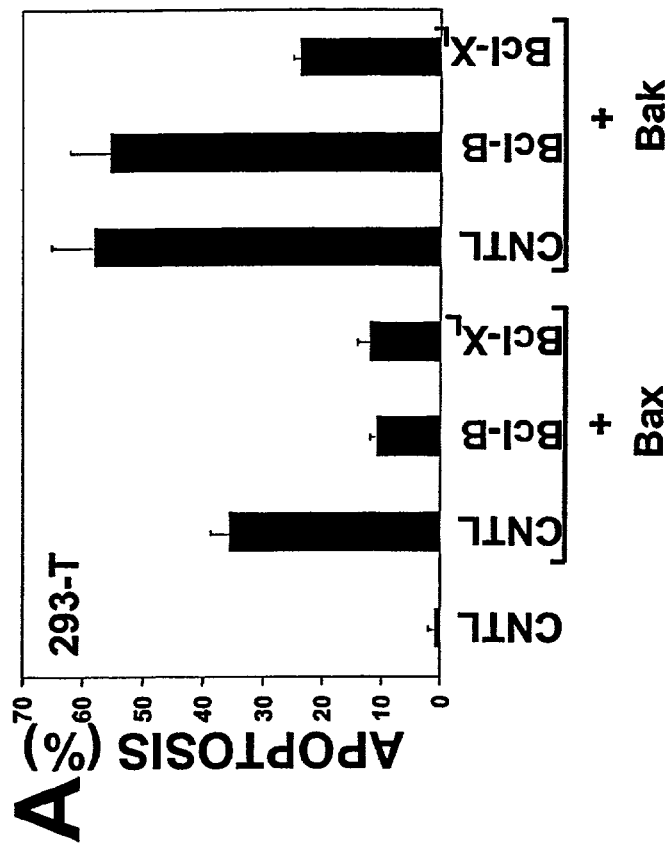

The cytoprotective activity of Bcl-B was studied by ascertaining the effect of Bcl-B expression on apoptosis induced by the pro-apoptotic proteins Bax and Bak. Co-expressing Bcl-B markedly suppressed apoptosis induced by Bax but not Bak (FIG. 3), thus correlating the protein-binding data indicating that Bcl-B binds Bax but not Bak (FIG. 2). Bcl-B mediated apoptotic suppression was not due to reduced levels of Bax protein, as determined by immunoblotting. In contrast to Bcl-B, co-expression of Bcl-$X_L$ suppressed apoptosis induced by either Bax or Bak (FIG. 3). Thus, Bcl-B appears to be functionally distinct from Bcl-XL.

Binding studies confirmed that binding between Bcl-B and Bax mediates suppression of apoptosis by Bax. In brief, HEK293T cells were transiently transfected with several Myc-tagged constructs (human calcyclin-binding protein, wildtype Bcl-B, L86A, R96Q, FFR(169-171)AAA, Δ118-133) and cell lysates were prepared and immunoprecipitated with anti-Myc antibody conjugated to beads. Immunoprecipitates were subjected to SDS-PAGE/immunoblot analysis using rabbit polyclonal antibodies specific for Bax (FIG. 4A). To confirm expression of proteins, lysates were subject to immunoblot analysis using antibodies specific for Bax and Myc.

For caspase assays, 293T cells were co-transfected with 0.5 µg of Bax and 1.0 µg of various Bcl-B constructs. Cell lysates were prepared 24 hrs after transfection, normalized for protein contents (25 µg), and incubated with 100 µM DEVD-AFC. Enzyme activity was determined by the release of AFC-fluorescence (FIG. 4B).

Figure 4:
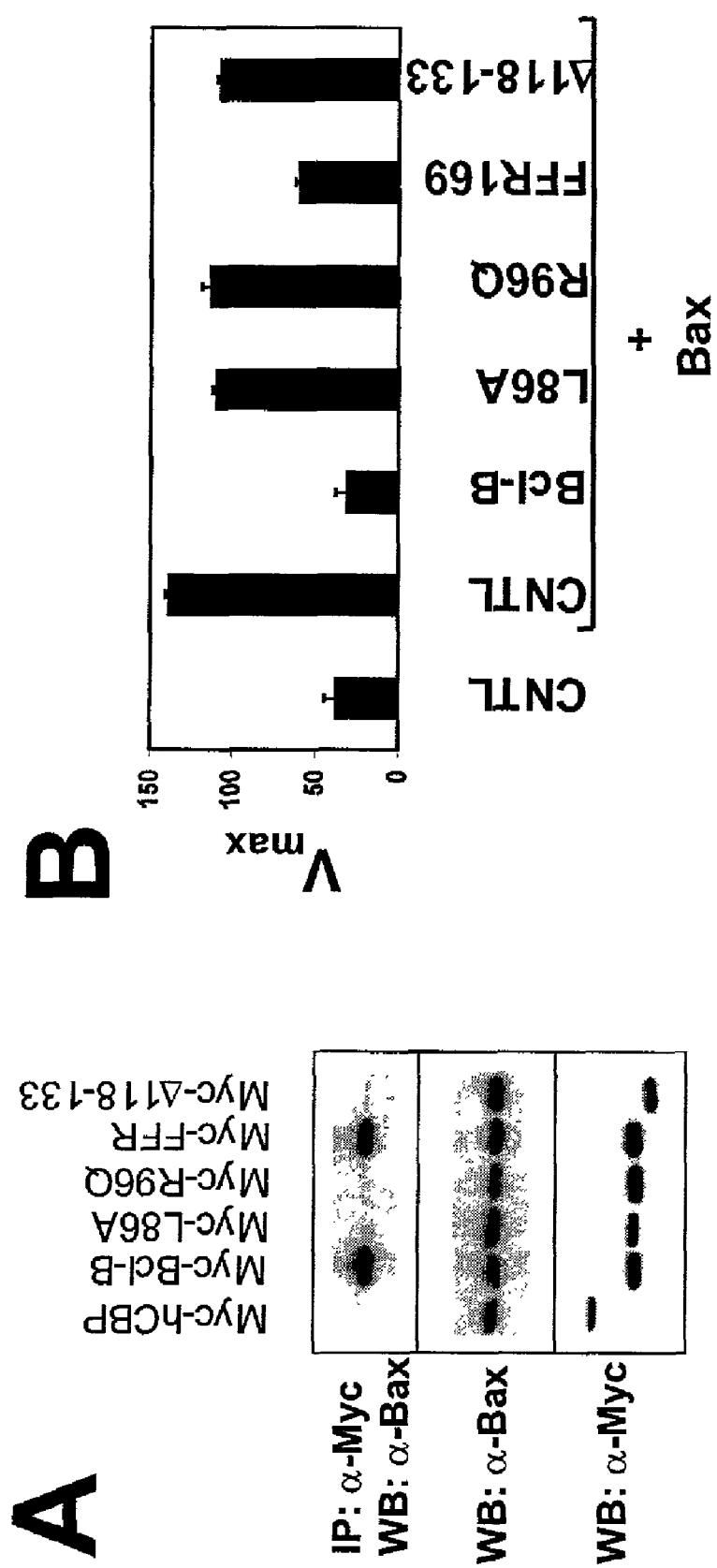
FIG. 4 shows that Bcl-B binding with Bax correlates with protection from apoptosis. (A) 293T cells transiently transfected with Myc-tagged constructs (human calcyclin-binding protein, wildtype Bcl-B, L86A, R96Q, FFR(169-171)AAA, Δ118-133), immunoprecipitated with anti-Myc antibody and subject to immunoblot analysis using antibodies specific for Bax. (B) caspase assays of 293T cells co-transfected with Bax and the Bcl-B constructs. Enzyme activity was determined by the release of AFC-fluorescence.

The results in FIG. 4 indicate that Bcl-B binding to Bax (Bcl-B wild type and FFR mutant) correlate with decreased caspase activity, whereas the three Bcl-B mutants L86A, R96Q and Δ118-133 that failed to bind Bax did not alter caspase activity (compare Myc-Bcl-B to Bcl-B and myc-FFR to FFR169 in FIGS. 4A and 4B). This data confirms that binding of Bcl-B to Bax mediates the protective activity of Bcl-B in Bax mediated apoptosis.

EXAMPLE 5

This example describes data showing that Bcl-B associates with mitochondria. This example also describes data showing that the C-terminal transmembrane (TM) domain of Bcl-B is important for efficient membrane targeting and function.

A plasmid encoding Green Fluorescent Protein (GFP)-tagged Bcl-B (GFP-Bcl-B) was transfected into Cos-7 cells as described in Example 1. Two-color confocal microscopy revealed a punctate cytosolic pattern and partial co-localization of GFP-Bcl-B with a mitochondria-specific dye (Mi-toTracker) (FIG. 5A). In contrast, cells transfected with GFP control protein produced diffuse cellular fluorescence.

To further evaluate location of Bcl-B, 293T cells were transfected with pcDNA3-Myc-Bcl-B, pcDNA3-Myc-Bcl-BΔTM, or pRC-CMV-Bcl-2 as described in Example 1. Subcellular fractionation analysis revealed that the Myc-tagged Bcl-B protein resides predominantly in the mitochondria-containing heavy-membrane (HM) fraction, similar to Bcl-2, as determined by immunoblot analysis of the cellular fractions (FIGS. 5B,C). In contrast to full-length Bcl-B, a truncation mutant of Bcl-B lacking the carboxylterminal TM domain (Bcl-BΔTM) targeted less efficiently to the HM fraction (FIG. 5D). The Bcl-BΔTM protein also was ineffective at suppressing Bax-induced apoptosis (FIG. 5E), even though this protein was produced at comparable levels to the full-length Bcl-B protein. Thus, efficient organellar targeting appears to be required for the apoptosis inhibiting activity of Bcl-B.

Figure 5:
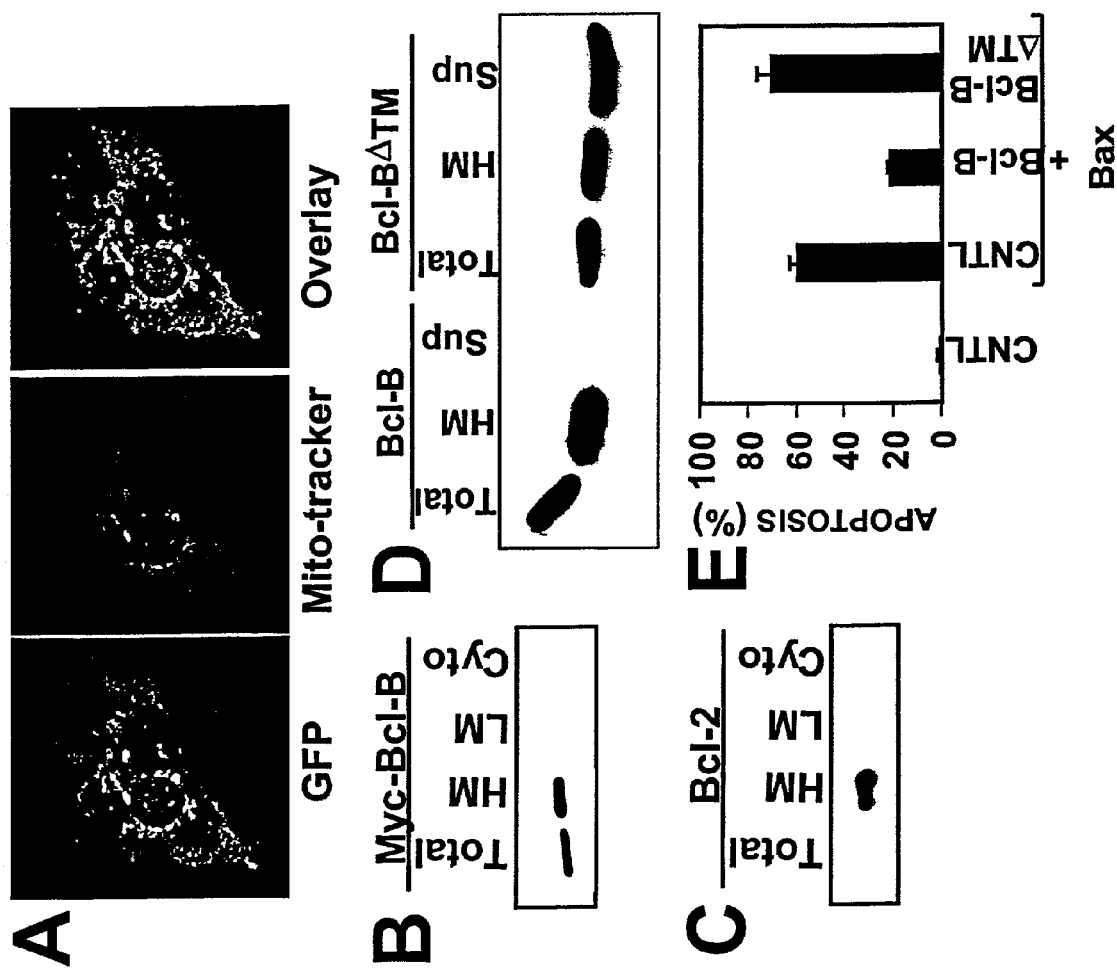
FIG. 5 shows that the C-terminal transmembrane (TM) domain of Bcl-B mediates efficient membrane targeting and is important for modulating apoptosis. (A) Confocal microscopy analysis of GFP-Bcl-B transfected Cos-7 cells. (B, C, D) 293T cells were transfected with (B) Myc-Bcl-B, (C) Bcl-2, and (1)) Myc-Bcl-B or Myc-Bcl-BΔTM. (E) 293T cells co-transfected with GFP (used as a marker for transfection) and either pcDNA3 (control; CNTL) or pcDNA3-Bax, in combination with a 2-fold excess of pcDNA3 (control), pcDNA3Myc-Bcl-B or pcDNA3-Myc-Bcl-BΔTM. The percentage of green cells with apoptotic morphology was determined (mean±SD; n=3).

For FIG. 5, at 24 hr post-transfection, cells were collected, and post-nuclear lysates prepared ("total"). An aliquot of these lysates was then fractionated by differential centrifugation at 10,000×g to pellet heavy membranes (HM). The resulting supernatant ("sup") was then either analyzed directly or subjected to centrifugation at 150,000×g to pellet light membranes (LM) and achieve a cytosolic supernatant. Proteins from each fraction were normalized relative to cell numbers and subjected to SDS-PAGE/immunoblot analysis using antibodies specific for Myc or Bcl-2. FIG. 5E, 293T cells were co-transfected with a plasmid encoding GFP (used as a marker for transfection) and either pcDNA3 (control; CNTL) or pcDNA3-Bax, in combination with a 2-fold excess of pcDNA3 (control), pcDNA3Myc-Bcl-B or pcDNA3-Myc-Bcl-BΔTM. Cells were collected and stained with DAPI after 24 hrs.

Expression of Green Fluorescent Protein (GFP)-tagged Bcl-B in cells revealed a punctate cytosolic pattern and partial co-localization with a mitochondria-specific dye (MitoTracker), as determined by two-color confocal microscopy (FIG. 5A). Crude subcellular fractionation analysis revealed that Myc-tagged Bcl-B protein resides predominantly in the mitochondria-containing heavy-membrane (HM) fraction, similar to Bcl-2, as determined by immunoblot analysis of the cellular fractions (FIGS. 5B,C). In contrast to full-length Bcl-B, a truncation mutant of Bcl-B lacking the carboxylterminal TM domain (Bcl-BΔTM) targeted less efficiently to the HM fraction (FIG. 5D). The Bcl-BΔTM protein also was ineffective at blocking Bax-induced apoptosis (FIG. 5E), even though this protein was produced at comparable levels to the full-length Bcl-B protein. Thus, efficient organellar targeting appears to be required for optimal function of Bcl-B.

These results demonstrate that Bcl-B associates with mitochondria. This is not an unexpected finding given that many Bcl-2 family proteins associate with mitochondria in cells (Reed, J. *Oncogene* 17, 3225-3236(1998); Reed, J. C. *Amer J Pathol* 157, 1415-1430(2000)).

A number of embodiments of the invention have been described. Nevertheless, it will be understood that various modifications may be made without departing from the spirit and scope of the invention. Accordingly, other embodiments are within the scope of the following claims.

What is claimed is:

1. An isolated or recombinant nucleic acid comprising a polynucleotide sequence that is 95% or more identical to SEQ ID NO:1, wherein said polynucleotide sequence encodes a polypeptide that is an apoptosis inhibitor.

2. The isolated or recombinant nucleic acid of claim 1, that is 95% identical to SEQ ID NO:1.

3. The isolated or recombinant nucleic acid of claim 1, wherein the sequence is attached to a substrate.

4. An expression cassette, comprising a polynucleotide sequence that is 95% or more identical to SEQ ID NO:1 operably linked to an expression control element, wherein said polynucleotide sequence encodes a polypeptide that inhibits apoptosis.

5. The expression cassette of claim 4, wherein the expression control element comprises a promoter or enhancer.

6. The expression cassette of claim 4, wherein the expression control element is constitutive, inducible, tissue-specific or developmentally related.

7. A vector comprising the expression cassette of claim 4.

8. The vector of claim 7 wherein said vector confers expression in bacteria, plant, insect, mammalian, or yeast cells.

9. The vector of claim 7 wherein said vector is a viral vector.

10. The viral vector of claim 9 wherein said vector said vector is an adenoviral vector.

11. The vector of claim 7 wherein said vector wherein the polypeptide encoded by the expression cassette comprises SEQ ID NO:2.

12. An isolated transformed cell comprising the nucleic acid of claim 1.

13. The isolated transformed cell of claim 12, wherein the cell is a bacteria, plant, insect, mammalian or yeast cell.

14. The isolated transformed cell of claim 12, where the cell is a mammalian cell and where the mammalian cell is human.

15. A method of producing a polypeptide comprising expressing a nucleic acid sequence that is at least 95% identical to SEQ ID NO:1, wherein the nucleic acid sequence encodes a polypeptide that inhibits apoptosis and said nucleic acid is expressed in solution, or in a cell in vitro.

* * * * *